(12) United States Patent
Shepler et al.

(10) Patent No.: US 12,115,235 B2
(45) Date of Patent: Oct. 15, 2024

(54) COMPOSITIONS, SYSTEMS, AND METHODS FOR ORAL DELIVERY

(71) Applicant: ULTRADENT PRODUCTS, INC., South Jordan, UT (US)

(72) Inventors: Brittany Shepler, Cottonwood Heights, UT (US); Andy Kawamoto, Sandy, UT (US)

(73) Assignee: ULTRADENT PRODUCTS, INC., South Jordan, UT (US)

( * ) Notice: Subject to any disclaimer, the term of this patent is extended or adjusted under 35 U.S.C. 154(b) by 0 days.

(21) Appl. No.: 18/163,060

(22) Filed: Feb. 1, 2023

(65) Prior Publication Data
US 2023/0240949 A1    Aug. 3, 2023

Related U.S. Application Data

(60) Provisional application No. 63/305,766, filed on Feb. 2, 2022.

(51) Int. Cl.
*A61K 8/04* (2006.01)
*A61K 8/81* (2006.01)
(Continued)

(52) U.S. Cl.
CPC ............ *A61K 8/042* (2013.01); *A61K 8/8147* (2013.01); *A61K 8/8182* (2013.01); *A61K 8/89* (2013.01);
(Continued)

(58) Field of Classification Search
None
See application file for complete search history.

(56) References Cited

U.S. PATENT DOCUMENTS

| 5,006,340 A | 4/1991 | Atsuta et al. |
| 5,310,563 A | 5/1994 | Curtis et al. |

(Continued)

FOREIGN PATENT DOCUMENTS

EP    1258239 B1    11/2002

OTHER PUBLICATIONS

International Search Report and Written Opinion received for PCT Patent Application No. PCT/US23/61839, mailed on May 23, 2023, 11 pages.

(Continued)

*Primary Examiner* — Dominic Lazaro
(74) *Attorney, Agent, or Firm* — Workman Nydegger

(57) ABSTRACT

The disclosure relates to oral delivery compositions that transition from a flowable state to a hardened or semi-hardened state. The flowable hardening composition may be delivered to oral tissues, including teeth and/or gums, directly or using a barrier strip or a tray-like device. Such compositions may be configured as a multi-part system wherein reactive materials (e.g., catalyst and reactive resins) are kept separate until use. Dispersion of the agents in a viscous carrier within the hardened composition enables a gradual release the desired agent(s) to reduce or eliminate sensitivity that may be caused by certain agents (e.g., dental whitening agents). The hardened delivery composition may include a reverse image of the oral tissue, allowing it to be removed and replaced multiple times during a single use, giving users more flexibility during treatment.

20 Claims, 12 Drawing Sheets

(51) Int. Cl.
*A61K 8/89* (2006.01)
*A61Q 11/00* (2006.01)

(52) U.S. Cl.
CPC .......... *A61Q 11/00* (2013.01); *A61K 2800/58* (2013.01); *A61K 2800/594* (2013.01); *A61K 2800/92* (2013.01); *A61K 2800/95* (2013.01)

(56) References Cited

U.S. PATENT DOCUMENTS

| | | | |
|---|---|---|---|
| 5,501,727 | A | 3/1996 | Wang et al. |
| 6,455,608 | B1 | 9/2002 | Jia et al. |
| 6,488,913 | B2 | 12/2002 | Orlowski et al. |
| 6,503,485 | B1 | 1/2003 | Allred |
| 9,044,288 | B2 | 6/2015 | Angeletakis |
| 9,278,064 | B2 | 3/2016 | Avramoff et al. |
| 2004/0028624 | A1* | 2/2004 | Bublewitz .............. A61Q 11/00 424/53 |
| 2006/0052471 | A1 | 3/2006 | Ashman et al. |
| 2009/0087812 | A1* | 4/2009 | Andersen ............. A61C 19/066 433/37 |

OTHER PUBLICATIONS

International Search Report and Written Opinion received for PCT Patent Application No. PCT/US23/61839, mailed on Aug. 15, 2024, 8 pages.

\* cited by examiner

COMPOSITIONS, SYSTEMS, AND METHODS FOR ORAL DELIVERY

CROSS REFERENCE TO RELATED APPLICATION

This application claims the benefit of U.S. Provisional Application No. 63/305,766, filed Feb. 2, 2022, which is incorporated by reference in its entirety.

TECHNICAL FIELD

This disclosure relates to compositions for oral delivery, and related systems and methods. Such compositions may include a curable material combined with a functional agent in a carrier and may be introduced to any oral tissue, including the teeth, gums and/or buccal tissue, in a flowable state prior to curing or setting to a hardened state.

RELATED TECHNOLOGY

Delivery of treatment agents to oral tissues, including soft tissues and teeth, can be performed using a variety of systems including oral rinses, toothpastes, gels, varnishes, and tablets.

For example, cosmetic tooth whitening products are conventionally delivered via fluid gels using trays or disposable strips. Such whitening gels are often sticky and typically require the user to clean their teeth after use. In cases where the product is applied to teeth using a reusable custom tray, the tray must also be cleaned between uses. Further, if the tray (custom or not) has a poor fit, the user may experience discomfort during the treatment process, and whitening gel may spill out of the tray onto the user's gums or other soft oral tissue, exacerbating the discomfort. This discomfort may last for a few days. These problems make the products inconvenient to use and can deter compliance by some users.

Some whitening systems, such as disposable strips, are relatively easy to apply and can be purchased over the counter. However, they usually have relatively low concentrations of whitening ingredients and are only intended for short, single-use applications. Using strips creates drawbacks, such as requiring a longer whitening program with a higher number and frequency of applications. Users can also still have residue on their teeth after whitening using whitening strips and thus still need to clean the teeth after removing the strip. The disposable strips may also slide around during the single-use application. This can expose the user's gums to the whitening agent (typically a peroxide), which can cause increased gum sensitivity. Dislodgement of the strip also means the teeth may not be optimally whitened, which is the purpose of using the strips.

Treatment of gum disorders, such as periodontal pockets, may be performed using mouth rises or dissolvable intra-pocket devices lodged into a periodontal pocket. However, mouth rinses may not effectively reach the pockets, and inter-pocket devices may cause discomfort and dissolve before effective treatment time is reached.

Ultimately, the main impediment to successful delivery of agents to oral tissues is the failure of the user to properly complete the prescribed treatment regimen. If the treatment apparatus is uncomfortable to wear, difficult to use or install, and/or is prone to prematurely dislodge from the user's teeth, the user may simply give up and prematurely abort the prescribed regimen. Thus, even if dental treatments are possible using a particular treatment apparatus or method, they are less likely to be properly completed if the inadequacies of the treatment apparatus or method cause a user to lose interest before the desired results are attained.

SUMMARY

The present disclosure relates to improved compositions and systems for delivering a functional agent to teeth and/or oral tissue, which overcome the above-mentioned disadvantages of conventional devices, and methods for oral delivery that provide simple, quick, inexpensive, even, and reusable application.

In general, the composition includes a fluid or viscous carrier for the functional agent, such as a water-soluble polymer carrier, dispersed in a hardening or curing system, such as elastomeric impression materials (e.g., polyvinylsiloxane) and curable resin systems (e.g., acrylates, methacrylates, epoxies, and polyurethanes). For example, the treatment composition may be a multi-part (e.g., two-component) composition, wherein one part includes one or more functional agents and one or more catalysts and/or initiators, and another part includes reactive components, such as silicone-based condensation chemistry ingredients or reactive monomers.

Storing the catalyst with the functional agents (e.g., tooth whitening, tooth desensitizing, and/or oral treatment agents) and isolating the catalyst or initiator from the reactive, hardening ingredients prevents premature curing and, therefore, is a new method of maintaining stability of such ingredients. For example, the inventive composition may maintain stability for several months to a year or more. In some embodiments, a whitening agent is included alongside a viscous carrier material. Dispersing the functional agent in the carrier material facilitates movement of the agent through the composition after curing, thereby enabling efficient delivery of the agent to the desired tissue. The functional agent and the carrier material may be mixed prior to combining them with the agent such that at least a portion of the agent remains dispersed within the carrier material within the composition.

In use, components within the curable material undergo a curing or setting process (e.g., a chemical or physical curing process) when they are mixed together. For example, the material may include reactive resins that, in the presence of the catalyst or initiator and/or moisture, crosslink to initiate curing. The reactive resins may be kept separate from the catalyst in the multi-part system. Each part of the multi-part system may advantageously be flowable to facilitate mixing to form the curable treatment material. Once formed, the curable material may remain flowable for a length of time sufficient for delivery to teeth and/or soft oral tissue. In this way, the curable composition advantageously becomes a single solid or semi-solid coherent mass after the two parts have been mixed and allowed sufficient time to cure and/or harden.

The disclosed compositions, methods, and systems provide oral and dental care products that are at least as stable and effective as conventional products while also being more convenient and comfortable to use. In some embodiments, an oral or dental composition is formed as a gel that undergoes a chemical cure process after mixing and application to oral tissue and turns into an elastomeric solid. In some embodiments, the composition can be applied directly to teeth or other oral tissue. In other embodiments, the gel may be placed in or on a support or delivery device, such as a backing strip or tray-like device, prior to curing. Such a tray-like device may be a conventional dental whitening tray, which may be customized or non-customized. The delivery device having the gel thereon may be placed onto a user's oral tissue, such as the teeth and/or dental arch. The gel may cure into an elastomer having therein an impression or imprint of the portions of the user's teeth and/or dental arch in contact with the gel. For example, the elastomer may be a translucent or clear membrane that includes a reverse image of the user's dentition and/or dental arch. Advantageously, the hardened elastomeric gel can also be removed and reinstalled multiple times during a single use, giving users more flexibility while treating their teeth.

The curing or hardening behavior of the treatment gel may be achieved, for example, using a two-part condensation cure silicone chemistry. In the presence of water and the catalyst or initiator, reactive silicone materials present in the treatment composition undergo hydrolysis and begin to crosslink. This transforms the gel components into an elastomeric solid.

A non-limiting example formulation of a silicone-based hardening delivery composition is as follows:
  Part A: silanol-terminated silicone polymer(s) (e.g., hydroxy-terminated polydimethylsiloxanes), functional silane(s) (e.g., silicate esters), and optional additives (e.g., fillers, surfactants, etc.)
  Part B: condensation catalyst (e.g., organotin compounds), functional or treatment agent (e.g., tooth whitening, desensitizing and remineralizing agents, and/or periodontal treatment agents), carrier material (e.g., polyacrylic acid, polyvinylpyrrolidone, etc.), additives (e.g., fillers, surfactants, etc.)

The formulation of the multiple parts of the multi-part composition may play an important role in maintaining a viable and stable product. It has been demonstrated that separating the reactive materials (i.e., the silicone polymer and the crosslinker) from the catalyst or initiator prevents premature curing of the composition, enabling long-term storage and subsequent use. For example, parts A and B of the example formulation above may be formulated as flowable compositions that may be readily mixed to form a flowable gel-like composition. Part A may be mixed with Part B to initiate the curing reaction to convert the flowable gel composition into a hardened (yet advantageously flexible and resilient) treatment composition. The two parts may, for example, be loaded into a delivery system that contains two chambers, such as a dual-barrel syringe (e.g., side-by-side or concentric). The two parts may be expressed through a mixing tip to mix the components together and produce a gel in which the treatment agent and the carrier material are substantially homogeneously dispersed throughout the reactive chemistry.

In its uncured or partially uncured state, the mixture may be flowable and be applied directly to oral tissue or applied to teeth or other oral tissue using a delivery device, such as a backing material, oral treatment device, or dental treatment tray. When used, a dental tray containing the uncured or partially uncured mixture is placed over the teeth (and optionally gum tissue), or an oral strip having the uncured or partially uncured mixture thereon is placed on a region of teeth and/or other oral tissue, and the gel allowed to harden. As the reactive ingredients in the composition cure to a hardened state, the elastomeric material forms a reverse image or impression of where it is applied. Once removed, the hardened composition mirrors and maintains the shape of the teeth and/or surrounding tissue in a manner similar to dental silicone impression materials. The elastomeric behavior of the hardened composition allows the user to readily and cleanly remove it and leave little to no residue behind, and subsequently reapply it to the site of application to resume treatment (e.g., cosmetic tooth whitening, tooth desensitizing, or gum treatment) at a later time. While the hardened composition typically deforms when removed and/or reinstalled, because it is elastomeric, it will return to its original molded shape when a deformation force is removed.

The hardening or hardened treatment composition enables gradual release of functional or treatment agents from the combined silicone and polymer systems in comparison to conventional oral treatment compositions, such as desensitizing or whitening gels. Such gradual release of such agents can reduce sensitivity, such as sensitivity caused by tooth whitening agents (such as peroxides), by reducing the amount and/or concentration of whitening agent that would otherwise contact the teeth and surrounding soft oral tissue at a given time, while also extending the time in which the whitening agent remains active. Gradual release of these and other agents, such as potassium nitrate or fluoride tooth desensitizing agents, provides improved results. Extended release of such agents also enables a user to temporarily remove the composition to perform an activity, such as eating or brushing teeth, and later resume treatment using the same composition instead of having to use an additional amount of the composition.

The silicone-based chemistry is a non-limiting example polymer system that can be employed in this invention. Other curable chemistries can be used. For example, a formulation of a hardening methacrylate delivery composition is as follows:
  Part A: methacrylate resins and optional additives (e.g., amine synergists, light-activated initiators, fillers, surfactants, etc.)
  Part B: polymerization initiators (e.g., organic peroxide initiators), functional or treatment agents (e.g., tooth whitening, desensitizing and remineralizing agents, and/or periodontal treatment agents), carrier material (e.g., polyacrylic acid, polyvinylpyrrolidone, etc.), additives (e.g., fillers, surfactants, etc.)

A water-soluble polymer, such as polyacrylic acid and/or polyvinylpyrrolidone may also be included as a carrier material. The carrier material may act as a thickening agent or rheological modifier and promote even mixing of the components of the system. Without the addition of the carrier material, the component containing both the treatment agent and the catalyst or initiator may not readily mix with the other component containing the siloxane material(s) as is desired to create a homogeneous and functioning hardening gel. Inefficient or incomplete mixing may be particularly improved where the treatment agent is a liquid, such as hydrogen peroxide. The addition of carrier materials that are more hydrophilic than the siloxane materials may also improve retention and sustained release of the treatment agent.

Advantageously, the treatment agent is dispersed within cohesive mass once hardened, providing steady release of the agent to the teeth. To remove the hardened delivery material after a desired time period, the user may simply grasp a corner or portion of the adhered composition or barrier material on which the composition is disposed and pull it off the teeth. Generally, the hardened delivery material typically pulls away in a single coherent piece, greatly simplifying removal compared to conventional dental treatment gels. Typically, little to no residual material will remain adhered to the user's teeth and tissues after removal. The ability of the hardened delivery material to remain as a single coherent piece of material also permits it to be reapplied and reused.

In addition, the multi-part composition may advantageously exhibit a lag time between initial contact and/or mixing, and when the combined composition completes the setting process. Such a lag time provides the user sufficient time to place the composition over the teeth and/or other oral tissue while still in a flowable, manipulable condition so that if the composition is in a dental tray or on a strip, the teeth can be pressed into the mass to form an impression prior to complete setting.

These and other objects and features of the present invention will become more fully apparent from the following description and appended claims, or may be learned by the practice of the invention as set forth hereinafter.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

Figure 1:
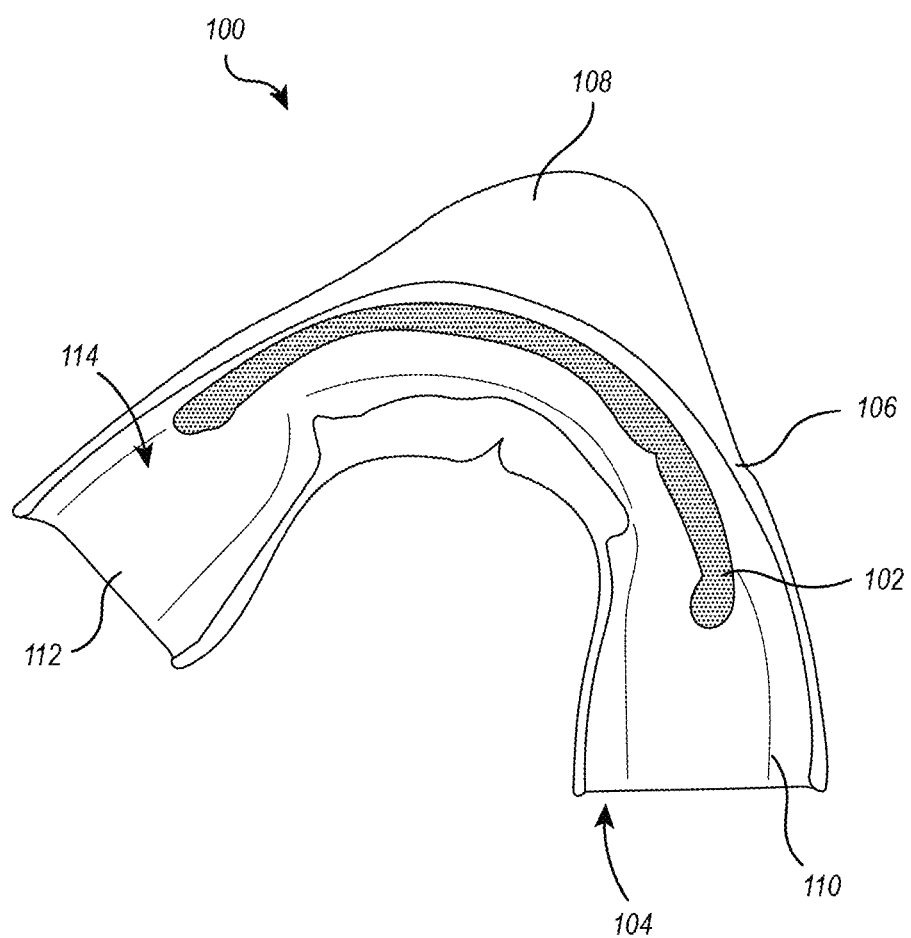
FIG. 1 illustrates a perspective view of an embodiment of a dental delivery system including a dental tray having a quantity of a curable whitening composition therein and configured to fit over at least a portion of an upper or lower dental arch.

The present disclosure relates to hardening or curable oral treatment compositions suitable for use in delivering functional agents to oral tissue(s). Such compositions may include, for example, a hardening or curable composition including at least one functional agent dispersed in a carrier material, which may be a polymer, a solvent, or combination thereof. The hardening material used in the composition may be a curable or setting material, while the carrier material may be a material that remains viscous.

The disclosed compositions, methods, and systems provide versatile and convenient delivery of agents to oral tissue. As used herein, "oral tissue" means and includes tissue in the mouth, pharynx and throat, including, but not limited to, teeth, gingiva (or gums), buccal tissue (e.g., cheek tissue), tongue, bone, blood vessels, nerves, and salivary glands. By way of non-limiting example, the hardening composition may be a chemically curing composition that includes multiple (e.g., two) parts, a first part, including the functional agent(s) alongside a catalyst, and another part including the remaining curing chemistry. In some embodiments, combining and storing the catalyst or initiator with the functional agents and isolating the catalysts from the reactive materials and/or crosslinkers is an example of an improved approach to maintaining the stability of the components prior to mixing and curing. In some embodiments, the treatment agents are combined with a carrier material, such as a water-soluble polymer.

For example, the hardening or curing composition may be a cosmetic tooth whitening, oral desensitizing, or periodontal treatment composition that is at least as stable and effective as conventional products while being more versatile and convenient. Specifically, the disclosed hardening or curing compositions improve ease of use by reducing or eliminating cleanup and user error, providing a more comfortable user experience, and enabling reuse of the composition once hardened. Such advantages promote compliance to prescribed treatment regimens. By comparison, conventional whitening, desensitizing, and periodontal treatments are non-curable, non-hardening gels that generally include a treatment agent dispersed in a viscous carrier. In contrast, the presently disclosed invention relates to a treatment composition that undergoes a curing or setting process, after mixing and application to teeth and/or other oral tissue(s) and is transformed into a solid or semi-solid material. The treatment composition may be directly placed in contact with oral tissue or teeth on its own or, alternatively, by means of a carrier, such as a tray-like device prior to curing. The hardened treatment composition can also be removed and reinstalled one or multiple times during a single use cycle, providing users more flexibility while treating their teeth without wasting and having to replace the treatment material with a quantity of new treatment composition, as is the case when using conventional treatment gels.

As used herein, the terms "harden" and "hardening" may refer to the transition of a viscous and/or fluid material or composition to an at least partially solidified or consolidated material or composition to form a "hard" or "hardened" material or composition. Such hardened material or composition may be substantially non-flowable or solid material and/or may substantially retain its three-dimensional shape without the need for external support. For example, the hardening material or composition may be any material capable of being cured or set to a hardened state (yet remain flexible and resilient).

The hardening material may be a curing material or resin, such as crosslinkable or polymerizable monomers, oligomers, or polymers, or a setting material. The hardening material may be hardened (cured or set) by physical action (e.g., by light, heat or pressure) or chemical action (e.g., catalyst, initiators or solvents). Examples of crosslinkable or polymerizable materials include, but are not limited to, siloxanes and polysiloxanes (e.g., polyvinylsiloxanes ("PVS"), hydroxypolydialkylsiloxanes), acrylates, methacrylates, acrylic acids, methacrylic acids, acrylamides, methacrylamides, aldehydes, vinyl acetate, methyl vinyl ether maleate, aziridines, vinyl ethers, epoxides, polyols, polyamines, di- and polyisocyanates, cyanoacrylates, polyethers, polyether-PVS hybrids, polysulfides, glass ionomer fillers, glass ionomer cements, zinc phosphate cements, carboxylate cements, cyclic amides, cyclic esters, silicate cements, silicophosphate cements, silicones, silicone rubbers, and combinations thereof. Elastomeric materials, such as polysulfides, polyethers, condensation-cured silicones (e.g., α-ω-hydroxyl-terminated polydimethyl siloxane), and addition-cured silicones (e.g., polyvinyl siloxane (PVS) or vinyl polysiloxane (VPS)), may be particularly useful as hardening materials. Examples of setting materials include, but are not limited to, alginate, alginic acids, agar, curdlan, gelatins, konjac glucomannan, methylcellulose, hydroxypropylmethyl cellulose, pectin, starches, carrageenans, Portland cement, and other hydrocolloids, gels and cements, and combinations thereof.

Examples of catalysts and initiators that may be used include metal salts (e.g., platinum and tin carboxylates such as dibutyltincarboxylates), organometallic compounds (e.g., organo titanates), amines (e.g., tertiary amines), dimorpholinpdiethyl ethers, radical initiators (e.g., peroxides of the general structure RO—OR, such as benzoyl peroxide, diisopropylbenzene monohydroperoxide, and camphorquinone).

The functional agent may be any substance that may be desirable to deliver oral tissue, such as a substance having a treatment, therapeutic, and/or cosmetic benefit. For example, functional agents may include, but are not limited to, tooth whitening agents, tooth mineralizing or treatment agents (e.g., desensitizing agents and remineralizing agents), therapeutic agents (e.g., chemotherapeutics), caries inhibitors (e.g., urea, calcium glycerophosphate, sodium trimetaphosphate, silicone polymers, plant extracts, etc.), chelating agents (e.g., EDTA, citric acid, alkali metal pyrophospates, polyphosphoric acid hydrochloric acid, phosphonates, etc.), anesthetic agents (e.g., benzocaine, lidocaine, etc.), cosmetic agents, antibiotics, antifungal agents (e.g., itraconazole, terbinafine, fluconazole, etc.), antimicrobial agents (e.g., tetracycline, triclosan, chlorhexidine, zinc nitrate, silver nitrate, copper, limonene, antimicrobial peptides (AMPs)), cetyl pyridinium salts, methyl benzoate, propyl benzoate, etc.), antiplaque and anti-tartar agents (e.g., pyrophosphates, antioxidants, quaternary ammonium compounds, phenols, copper salts, strontium salts, magnesium salts, zinc salts, anionic polymers, etc.), pain relief agents (e.g., ibuprofen, acetaminophen, epinephrine, menthol, or other analgesics), antioxidants and vitamins (e.g., vitamin A, vitamin E, vitamin C, etc.), breath freshening agents (e.g., zinc gluconate, zinc citrate, alpha ionone, etc.) and essential oils (e.g., eucalyptol, menthol, methyl salicylate, thymol, etc.).

The curable composition may be a tooth whitening composition that includes one or more tooth whitening agents (e.g., to provide cosmetic tooth whitening). Examples of useful tooth whitening agents include, but are not limited to, peroxy compounds, chlorine dioxide, chlorites and hypochlorites, percarbonates, metal chlorites, persulfates, perborates, etc. Examples of suitable peroxy agents include, but are not limited to, hydrogen peroxide, carbamide peroxide, peroxides of alkali and alkaline earth metals (e.g., lithium peroxide, potassium peroxide, sodium peroxide, magnesium peroxide, calcium peroxide, and barium peroxide), organic peroxy compounds, peroxy acids and salts thereof, and polymer-peroxide complexes (e.g., a polyvinylpyrrolidone-hydrogen peroxide complex such as Peroxydone™ complexes). Organic peroxy compounds include, for example, carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, monoperoxyphthalate and the like. Peroxy acids and their salts include organic peroxy acids such as alkyl peroxy acids and monoperoxyphthalate, as well as inorganic peroxy acid salts including persulfate, dipersulfate, percarbonate, perphosphate, perborate and persilicate salts of alkali and alkaline earth metals such as lithium, potassium, sodium, magnesium, calcium and barium. Another useful peroxy compound is sodium pyrophosphate peroxyhydrate. In some embodiments, the whitening agents may be included as a complex with the carrier material. For example, a complex of polyvinylpyrrolidone and hydrogen peroxide (e.g., Peroxydone™ complex) may be used in the hardening composition.

In some embodiments, a hardening tooth whitening composition may be formulated as a multi-part (e.g., two-part) dental treatment system that includes a tooth whitening agent in a polyvinylsiloxane elastomeric matrix. Such dental treatment composition may include a first part, including whitening and/or desensitizing agent(s) alongside catalyst(s), and a second part including the remaining condensation chemistry ingredients. As used herein, "remaining condensation chemistry ingredients" refers to reactive silicone polymers, such as silanol- or hydroxy-terminated siloxanes (e.g., hydroxy-terminated polydimethylsiloxanes), cross-linkers (e.g., multi-functional silanes and/or silicate esters), and/or other ingredients as appropriate.

One or more desensitizing or remineralizing may additionally be included in the tooth whitening composition. Suitable desensitizing and remineralizing agents may include, but are not limited to, nitrate ion sources (e.g., potassium nitrate and silver nitrate), fluoride ion sources (e.g., sodium fluoride, stannous fluoride, potassium fluoride, sodium fluorosilicate, ammonium fluorosilicate, and sodium monofluorophosphate), calcium ion sources and salts (e.g., calcium phosphate, calcium chloride, and calcium carbonate), potassium ion sources and salts (e.g., potassium nitrate and potassium citrate), phosphorous ion sources and salts (e.g., triethyl phosphate, calcium phosphate, and sodium phosphate), hydroxyapatite, fluorapatite, glutaraldehyde, zinc chloride, strontium chloride hexahydrate, strontium chloride, citrates, potassium oxalate, bio active glasses, and combinations thereof. Some desensitizing agents, such as fluoride, calcium and phosphate, can help strengthen the teeth and offset potential corrosive effects of peroxides on tooth enamel. In two-part compositions, the desensitizing agent may be included in one of the parts in an amount of up to about 85%, preferably up to about 50%, more preferably up to about 20%, such as in a range of from about 0.001% by weight to about 10% by weight of the composition.

The hardening or curing behavior may be completed, for example, using condensation cure silicone chemistries. In the presence of water and a catalyst or initiator, reactive silicone polymers undergo hydrolysis and begin to crosslink. This converts the liquid gel whitening material into an at least partially cured or set elastomeric material (i.e., an elastomeric solid). For example, the treatment material may be a curable polyvinylsiloxane composition including a silanol- or hydroxy-terminated siloxane, a crosslinker, a catalyst, and a treatment component.

Suitable silanol- or hydroxy-terminated siloxanes may include polydimethylsiloxanes, diphenylsiloxanes, polydiphenylsiloxanes, polytrifluoro-propylmethylsiloxanes, vinylmethylsiloxanes copolymers, and combinations thereof. In multi-part (e.g., two-part) compositions, the siloxane material may be included in one of the parts in an amount in a range of from about 20% by weight to about 95% by weight, preferably 40% by weight to about 95% by weight, and more particularly, from about 70% by weight to about 90% by weight of the composition.

Suitable crosslinkers may include multi-functional silanes, such as vinyl functional silanes, hydride functional silanes, alkoxy, acetoxy, ester, enoxy, or oxime silanes, and/or silicate esters. Examples of crosslinkers that may be used in the whitening material include, but are not limited to, vinylisopropenoxysilanes (e.g., vinyltriisopropenoxysilane, vinylmethyldiisopropenoxysilane, and products of partial hydrolysis-condensation thereof, such as, vinylisopropenoxypolysiloxanes), methyl triacetoxy silane, methyl trioxime silane, ethyltriacetoxysilane, methyltriacetoxy-silane, bis(triethoxysilyl)ethane, vinyltriacetoxysilane, vinyltrimethylsilane, methyltriethoxysilane, methyltrimethoxysilane, tetra-ethoxysilane, tetra-n-propoxysilane, methyltris(methylethylketoximino)-silane, and combinations thereof. In two-part compositions, the crosslinker may be included in one of the parts in an amount up to about 50%, preferably up to about 20%, and more preferably up to about 10% by weight, such as in a range of from about 3% by weight to about 15% by weight, and more particularly, from about 5% by weight to about 10% by weight.

Suitable catalysts or initiators may include tin compounds, platinum compounds, and metal-organics, such as organotin complexes, platinum complexes, peroxide initiators, and titanates. By way of non-limiting example, the catalyst or initiator may include one or more of dimethyl-dineodecanoatetin, bis(neodecanoate)tin, stannous octoate (bis(2-ethylhexanoate)tin), di-n-butyldilauryltin, dimethylhydroxy(oleate)tin, di-n-butylbis(2-ethylhexylmaleate)tin, di-n-butylbutoxychlorotin, dibutyltindiacetate (di-n-butyl-diacetoxytin), di-n-butylbis(2,4-pentanedionate)tin, dibutyltin dilaurate (di-n-butyldilauryltin), dibutyltin dioctoate, dioctyltin dilaurate, stannous acetate, di-octyl tin-bis, di-octyl-tin-bis, and combinations thereof. Other silicone catalysts may include chloride, ammonium, iodonium, palladium, or peroxide. Yet other catalysts may include lead, antimony, iron, cadmium, barium, manganese, zinc, chromium, cobalt, nickel, aluminum, gallium, germanium, titanium, or zirconium, which may be provided as a compound or complex so as to be a metal-containing catalyst. Such catalysts can be used for moisture-curable compositions, including silicone. In multi-part (e.g., two-part) compositions, the catalyst or initiator may be included in one of the parts in an amount in a range of about 0.001% to about 10% by weight, preferably in a range of about 0.1% to about 10% by weight, more preferably in a range of about 1% to about 6% by weight. The minimum concentration of catalyst is typically about 500 ppm, with amounts in a range of about 0.05% to about 0.5% being suitable in some cases.

The compositions disclosed herein exhibit efficient curing in the presence of peroxide whitening agents and, thus, solves curing inhibition issues associated with incorporating peroxide compounds into polymer systems. Suitable whitening agents may include peroxide compounds and peroxide complexes. Examples of whitening agents that may be used in the whitening material include, but are not limited to, hydrogen peroxide, carbamide peroxide, sodium perborate, sodium percarbonate, and combinations thereof. In two-part compositions, the whitening agent may be included in one of the parts in an amount of up to about 90%, preferably in a range of about 5% to about 70%, more preferably in a range of about 10% to about 50% by weight.

In addition to the treatment agent, the catalyst or initiator, and the reactive components, the hardening composition also includes a carrier material to act as a thickener or diluent for the treatment agent (which may be liquid or solid) and to facilitate dispersion of the ingredients of the treatment material upon mixing. In some embodiments, the carrier material remains in an uncured, fluid or flowable state within the composition after the hardening materials in the composition have set or cured. The carrier material may, therefore, form a fluid or flowable passive network throughout the hardening composition. The carrier material may include one or more water-soluble polymers or viscosity adjusting/thickening agents including, but not limited to, polyacrylic acid, a poly(N-vinyl lactam) (e.g., polyvinylpyrrolidone (crosslinked or uncrosslinked)), polyacrylates, polyacrylamides, polyethylene glycols, waxes, propylene glycols, polar solvents (e.g., water), fillers (e.g., fumed silica or fumed alumina), cellulose derivatives (e.g., carboxymethylcellulose), alginates, starch, starch derivatives, polyurethane thickening agents or polyacrylic acid copolymers of polyacrylic acid and polyacrylamide, polyvinylpyrrolidone-vinyl acetate copolymers, polyvinyl alcohol, polyethylene oxide (e.g., POLYOX™ resin), polyvinyl caprolactam, glycerin, and/or a polyoxazoline copolymer (e.g., poly (2-ethyl-2-oxazoline)). The carrier material may also be a complex of such a water-soluble polymer and a peroxide compound. In two-part compositions, the carrier material may be included in one of the parts in an amount of up to about 90% by weight, preferably up to about 50% by weight, more preferably in a range of about 1% to about 40% by weight, and most particularly in a range of about 2% to about 25% by weight.

For example, the treatment composition may be formed as a two-part elastomeric system that includes a first part (Part A) containing a silanol- or hydroxy-terminated siloxane and a crosslinker, and a second, separate part (Part B) including a catalyst or initiator, the treatment agent, and the carrier material. The placement of the ingredients within Parts A and B can play an important role in maintaining a viable and stable product, as will be discussed in further detail.

As another example, the treatment composition may be formed as a two-part resin system that includes a first part (Part A) containing methacrylate resins, and a second, separate part (Part B) including an initiator, the treatment agent, and the carrier material. In the event the methacrylate system is a light-curing system, light-activated initiators may be included in Part A or Part B of the system.

Additional additives, such as fillers, surfactants, buffering agents, thickening agents, colorants, flavorings, and other additives may optionally be included in the treatment composition. For example, viscosity-adjusting ingredients, such as the carrier material and/or fillers, may be added to Part B to aid in storage and mixing. Such carrier materials and/or fillers prevent fluid treatment agents from shearing out upon mixing enabling an evenly mixed composition to be produced.

The two components (Parts A and B) are stored separately until they are mixed together to form the curable treatment composition, which may be applied to teeth and/or other oral tissue prior to fully curing. As a non-limiting example, the treatment composition may be loaded into a storage and delivery system that contains multiple (e.g., two) chambers, such as a dual-barrel syringe or a coaxial syringe. In some embodiments, the components are expressed through a mixing tip to cause them to be mixed and produce a substantially homogeneous mixture, which can be applied directly to oral tissue or to a delivery device, such as a dental whitening tray or flexible barrier material (such as a dental treatment strip), to facilitate application to oral tissue. The delivery device with the curable composition is placed on the teeth and/or other oral tissue, and the composition is allowed to cure and harden. Alternatively, the multiple parts may be mixed and deposited onto the teeth or delivery apparatus manually or using any other known method of mixing and/or dispensing.

Because the treatment composition chemistry involves curable materials, such as elastomeric materials, the composition cures with a reverse image of the teeth and/or oral tissue where it is applied. That is to say, the treatment composition becomes customized to the unique shape of the user's teeth and dental arch during the curing process in a manner similar to conventional dental silicone impression materials. The hardening behavior allows the cured or partially cured treatment material to be cleanly and readily removed—often in a single or a few pieces—without leaving a residue or remnants of sticky gel on the teeth and oral tissue, as is the case with conventional whitening and/or desensitizing gels. In addition, the hardened treatment material enables reuse, if desired, by simply repositioning it back over the teeth to the site of application such that the dentition rests within the impression formed in the hardening treatment material during the curing process.

The carrier material may act as a viscosity adjusting additive (e.g., thickening agent), binder, and/or dispersant for ingredients in the system promoting even mixing between the ingredients to improve the ease of use and consistency. In a two-component system, the ingredients of the component containing both the treatment agent and the condensation catalyst may be too fluid to readily mix with the other component to create a homogeneous and functioning hardening composition. By incorporating the ingredients into the carrier material prior to mixing, homogeneity and consistency of the final, mixed product may be significantly improved.

The treatment composition contains a treatment agent, such as a tooth whitening agent (e.g., peroxide whitening agent) and/or a desensitizing agent (e.g., potassium nitrate), which is/are gradually released from the combined silicone and polymer (e.g., polyacrylic acid) system. The slow release of a peroxide whitening agent reduces sensitivity that may be caused by conventional whitening, such as by reducing the quantity and/or concentration of whitening agent exposed to the teeth and/or soft oral tissue at a given time, as well as allowing a user to temporarily remove the cured treatment composition from their teeth and then reinstall it, if desired, to resume treatment using the same composition.

Without being bound to any particular theory, it is believed that incorporation of the carrier material prior to curing inhibits the silicone reaction in a way that reduces the degree of crosslinking in comparison to a purely silicone system that does not include a carrier material. In comparative samples containing only silicone without the carrier material, migration of actives (e.g., peroxides or desensitizers) is reduced or eliminated. In this way, the inventive composition enables peroxides and desensitizing materials to more readily physically migrate out of the composition in a way that is not observed in a purely silicone system and that enables effective treatment.

The composition may additionally include one or more fillers including, but not limited to, silica material (e.g., fumed silica), alumina materials (e.g., fumed alumina), quartz, cristobalite, calcium silicate, zirconium silicate, montmorillonites, bentonites, zeolites, sodium aluminum silicate, metal oxide powder, such as aluminum or zinc oxides or their mixed oxides, barium sulfate, calcium carbonate, gypsum, diatomaceous earth, and/or glass materials (e.g., silanated glasses). Use of a hydrophobic filler, such as fumed silica or alumina particles or powders may further facilitate incorporation of the whitening agent into the curable polymer system. The filler may be included in the composition in an amount of up to about 85% by weight, preferably up to about 50% by weight, most preferably up to about 20% by weight, such as in a range of from about 0.5% by weight to about 15% by weight, and more particularly, from about 3% by weight to about 10% by weight.

The composition may include other dental treatment agents, additives, and adjuvants. Examples include, but are not limited to, plasticizers and humectants (e.g., glycerin and sorbitol), stabilizing agents (e.g., EDTA, acrylates copolymer, and polyvinylpyrrolidone), neutralizing agents (e.g., potassium hydroxide, sodium hydroxide, triethylamine, and triethanolamine), buffering agents (e.g., sodium hydroxide, sodium phosphate, and citric acid), solvents (e.g., water), surfactants (e.g., polyethylene glycols), thickeners (e.g., polyacrylate thickeners, xanthan gum, gellan gum, guar flour, alginate, carrageenan, carboxymethyl cellulose, bentonite, wellan gum, locust bean flour, agar-agar, tragacanth, gum arabic, pectins, polyoses, starch, dextrins, gelatins, and casein, ethylene oxide/propylene oxide copolymers (polyoxamers) and sodium lauryl sulfate), preservatives (e.g., dipotassium phosphate and sodium benzoate), other medicaments, flavorings, colorants, sweeteners (e.g., sorbitol, xylitol, and sucralose), and the like.

In some embodiments, a whitening agent may be incorporated into the inventive whitening composition as a premixed whitening gel formulation. The premixed gel composition may be combined, for example, with the catalyst or initiator and optional additives to form the catalyst-containing component of the two-part whitening composition. For example, a premixed whitening gel formulation may include the whitening agent and the carrier material (e.g., water-soluble polymers) and, optionally, one or more desensitizing and/or remineralizing agents, polar solvents (e.g., water), buffering agents, humectants, sweeteners, and/or flavorings. As a non-limiting example, the formulation may include a mixture of hydrogen peroxide and/or carbamide peroxide, polyacrylic acid, glycerin, water, silica, sorbitol, xylitol, flavoring, ethylene oxide/propylene oxide copolymer (e.g., polyoxamer), sodium lauryl sulfate, sodium benzoate, sodium hydroxide, sucralose, xanthan gum, and colorants. As another non-limiting example, the premixed formulation may include hydrogen polyvinylpyrrolidone, high molecular weight polyethylene glycol (e.g., PEG-8 and PEG-6), water, acrylates copolymer, sodium hydroxide, and sodium saccharin.

Advantageously, the whitening agent is dispersed within the coherent polymer mass once hardened, providing a steady and sustained supply of treatment agent to the desired site (e.g., to the teeth for whitening). To remove the hardened dental treatment composition after a desired time, the user simply grasps a corner or portion of the adhered composition and pulls it off the teeth. Generally, the composition pulls off in a single coherent piece, making removal very easy.

In addition, the multi-part curable composition may advantageously exhibit a lag time between initial contact and/or mixing and when the combined composition completes hardening. Such lag time gives the user time to place the composition over the teeth while still in a flowable, manipulable condition so that it can conform to a user's teeth and dental arch. If the composition is provided within a tray or on a strip, the teeth can be pressed into the mass prior to complete hardening. For example, the length of curing time for the composition may range from 10 seconds to an amount of time for the desired application, where the amount of time may be in a range of about 10 minutes to about 24 hours. The amount of time may be predetermined and may be, for example, in a range of from about 30 minutes to about 10 hours, from about 1 hour to about 5 hours, or from about 2 hours to about 4 hours.

FIG. 1 is a perspective view that schematically illustrates an embodiment of a dental whitening system 100 including a hardening or curable dental whitening composition 102 delivered using a dental treatment tray 104 configured to fit over at least a portion of an upper or lower dental arch (not shown). While the embodiments shown in FIGS. 1-6 illustrate delivery using a dental tray, it is to be understood that any method or device for delivery of a dental or oral composition could similarly be used according to the present invention. For example, the delivery device may include a strip of material such as those utilized in conventional dental whitening strips. Additionally, the material 102 referred to in the following embodiments may additionally or alternatively be a desensitizing composition that includes one or more desensitizing agents. Alternatively, the composition can be applied directly to teeth or other oral tissue without a tray or strip.

The dental treatment tray 104 optionally includes an exoskeleton support tray 106 that has a handle 108. The support tray 106 may have a curved shape approximating a shape of a human dental arch. Disposed on the exoskeleton support tray 106 is the barrier material, which is shown in the form of a liner 110. In some embodiments, the liner 110 may be a flexible or flimsy material that has the shape provided by the support tray 106. For example, the liner 110 may have a thickness of less than about 2 mm, such as between about 0.3 mm and about 1 mm, to enable to the support tray 106 to conform to teeth and oral tissues. In other embodiments, the liner 110 may have an arch shape that fits within the support tray 106. The support tray 106 (if present) is configured to be removed from the liner 110 after an impression layer (not shown) is formed using, for example, handle 108.

The delivery device, such as liner 110, may be formed from polymer materials, thermoplastic elastomers, waxes, or combinations thereof. For example, the liner 110 may be a material that is substantially impermeable to water, saliva, and/or one or more materials in the whitening material 102 (e.g., peroxide actives). As a non-limiting example, the liner 110 may be formed from a wax-based composition including a combination of one or more waxes and one or more polymers, such as a thermoplastic elastomeric polymer. Suitable waxes include, but are not limited to, petroleum-based waxes, such as microcrystalline wax, paraffin wax, and/or intermediate wax. Suitable polymers include, but are not limited to, polyolefins, polyesters, polyurethanes, thermoset elastomers, and mixtures thereof, such high density polyethylene, low density polyethylene, ultra-low density polyethylene, polypropylene, polytetrafluoroethylene, thermoplastic polyolefins, propylene-based elastomers, ethylene-vinyl acetate copolymer, ethylene-vinyl alcohol copolymer, polyvinyl acetate, polyvinyl alcohol, polyesters, polycarbonates, methacrylates, acrylates, polyamides, polyurethanes, polyvinyl chloride, synthetic rubber, phenol formaldehyde resin, neoprene, polystyrene, polyacrylonitrile, polyvinyl butyral (PVB), silicone elastomers, and thermoplastic elastomers (e.g., olefin-based elastomers, such as ethylene-, propylene- and butylene-based elastomers).

The liner 110 has a trough or channel 114 defining an inner, impression-receiving surface 112 configured to receive an oral treatment composition, such as whitening composition 102. The whitening composition 102 may be disposed on the impression-receiving surface 112, which allows the whitening composition 102 to directly contact teeth at a site of application. As shown in FIG. 1, the whitening composition 102 may be dispensed as a bead or column in an amount sufficient to cover areas of the teeth where whitening (e.g., cosmetic) is desired and/or to obtain a mirror image or impression of the teeth or dentition as the whitening composition 102 hardens and cures.

In some embodiments, the whitening composition 102 is a two-part, silicone-based whitening composition, where a first part includes whitening agent(s) alongside a condensation catalyst, and the second part (which is separate from the first part) includes the remaining condensation chemistry ingredients. In some embodiments, the dental whitening composition 102 may be a curable polyvinylsiloxane-based system having two parts as follows:

Part A: silanol-terminated siloxane, multi-functional silane (e.g., silicate esters), and optional additives (e.g., fillers, surfactants, etc.);

Part B: condensation catalyst (e.g., organotin compounds), carrier material (e.g., polyacrylic acid), whitening agent (e.g., hydrogen peroxide, carbamide peroxide) and/or desensitizing agent, carrier material (e.g., polyacrylic acid, polyvinylpyrrolidone, etc.), and optional additives (e.g., fillers, surfactants, etc.).

In such a two-part system, the first part (e.g., Part A) and the second part (e.g., Part B) are mixed to form the hardening whitening composition 102.

Part A may include the siloxane material in an amount in a range of from about 0% by weight to about 100% by weight, and more particularly, from about 25% by weight to about 90% by weight, the crosslinker in an amount in a range of from about 0.5% by weight to about 40% by weight, and more particularly, from about 2% by weight to about 25% by weight. The concentration of siloxane and crosslinker materials may be adjusted to achieve desired material properties, such as viscosity, setting behavior, and hardness of set material. Part B may include the catalyst in an amount in a range of from about 0.001% by weight to about 20% by weight, and more particularly, from about 0.05% by weight to about 10% by weight, the whitening (and/or desensitizing agent) in an amount in a range of about 1% to about 70% by weight, and more particularly, from about 10% to about 60% by weight, the carrier material in an amount in a range of about 1% to about 100% by weight, and more particularly, from about 1% to 25% by weight.

Optional additives that may be included in Part A or B include carrier/filler materials, dental treatment agents, additives, and adjuvants, such as those previously discussed herein. For example, the additives may include carrier materials, fillers, surfactants, and/or other thickening agents, as well as buffering agents, colorants, flavorings, and other additives. For example, the filler may be included in one or both of Parts A and/or B in an amount in a range of from about 2.5% by weight to about 5% by weight, while the carrier material may be included in an amount in a range of from about 5% by weight to about 20% by weight.

Figure 2:
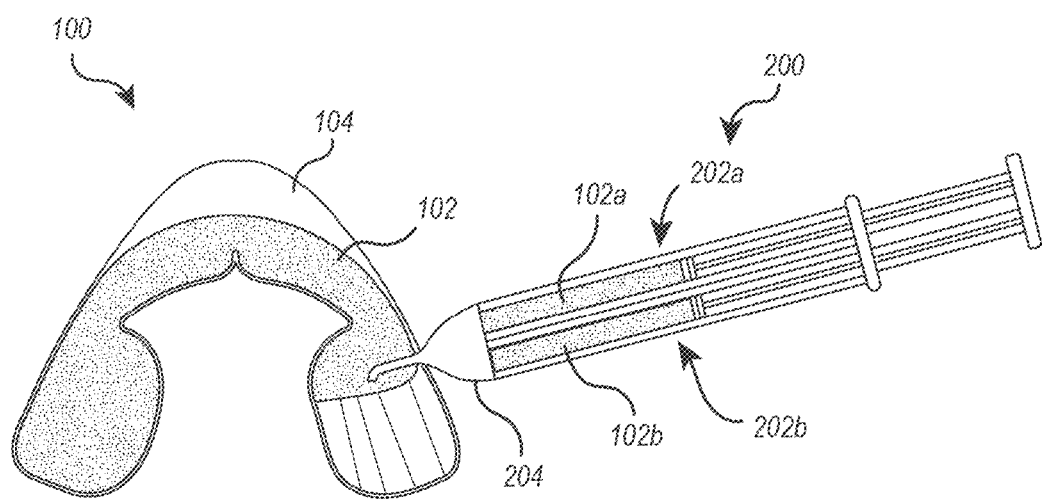
FIG. 2 illustrates an embodiment of applying the curable whitening composition to the dental tray to form the dental delivery system as shown in FIG. 1.

For example, as shown in FIG. 2, Part A (102a) and Part B (102b) may be separately loaded into the different barrels 202a and 202b of a double-barreled syringe 200 and may be expressed through and mixed within a mixing tip 204 before being dispensed into the dental tray 104. As Parts A and B are expressed from the compartments of barrels 202a and 202b through the mixing tip 204 of the syringe 200, the ingredients of Parts A and B are mixed together to produce a substantially homogeneous whitening material 102. The whitening composition 102 may be placed into the tray 104 as desired, for example, it may be dispensed onto inner surfaces 112 of the tray 104 as shown, as a string- or bead-like structure as shown in FIG. 1, or to substantially fill at least a portion of the tray 104.

The separate parts, Parts A and B, may be mixed in various ratios depending on the desired material properties. For example, Parts A and B may be combined in a ratio in a range of 1:10 to 10:1, such as in a ratio of 1:1, 1:2, 1:3, 3:1, or 2:1

Once mixed, the whitening composition 102 disposed in the tray 104 begins to harden and cure. For example, in the polyvinylsiloxane system, the reactive silicone materials from Part A undergo hydrolysis and begin to form siloxane crosslinks in the presence of moisture and the catalyst from Part B. The curing reaction is not so fast as to prevent a user from pressing the teeth into the whitening material 102. For example, the whitening composition 102 may still be in a flowable or semi-flowable state in which the teeth may be placed into contact with or submerged therein for a length of time in a range of from about 10 seconds to about one hour.

Figure 3:
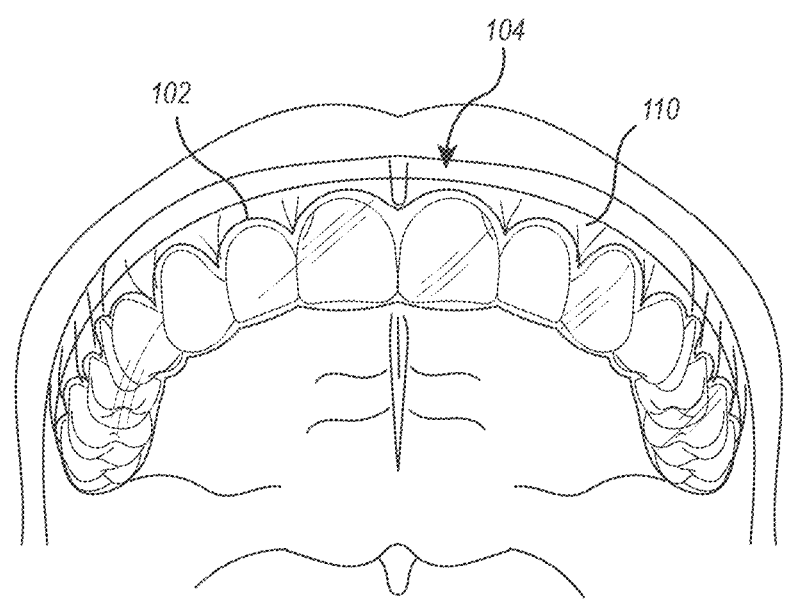
FIG. 3 illustrates the dental delivery system after it has been placed over teeth of a dental arch causing the curable whitening composition to conform thereto.

As shown in FIG. 3, the dental tray 104 containing the whitening composition 102 dispensed therein is placed inside the oral cavity of a user and over the teeth. The whitening composition 102 may be placed into direct contact with surfaces of the teeth such as by pressing a lower surface of the tray 104 towards the teeth to bring at least a portion of the teeth into contact with the uncured or partially uncured whitening composition 102. The exoskeleton support tray (not shown), if present, may be removed from the inner tray or liner 110. The liner 110, containing the whitening composition 102, remains disposed over or connected to the whitening composition 102 to provide support and to prevent the whitening composition 102 from coming into contact with surrounding oral tissues. While FIG. 3 illustrates a non-customized dental tray 104 placed over the upper teeth, it is to be understood that a customized dental tray having contours customized to the upper teeth or barrier material could alternatively be employed, and that the method could be similarly used on lower teeth. The dental tray 104 is shown as being transparent for the purposes of illustrating the underlying whitening composition 102 and teeth, the dental tray 104.

Placement of the dental tray 104 over the dental arch such that the teeth contact causes the uncured or partially cured whitening composition 102 to conform to the shape and contours in the teeth while the whitening composition 102 is in a flowable state. The whitening composition 102 inside the dental tray 100 will continue to cure after being placed over the dental arch and teeth. As the whitening composition 102 undergoes curing, a reverse image of portions of the user's teeth and dental arch is captured therein due to the nature of the silicone-based materials in the whitening composition 102. Thus, the dental whitening composition 102 becomes customized to the teeth placed into contact with the whitening composition 102. As the whitening composition 102 continues to cure, the whitening agent will be gradually released from the whitening composition 102 to the teeth in a sustained manner.

Figure 4:
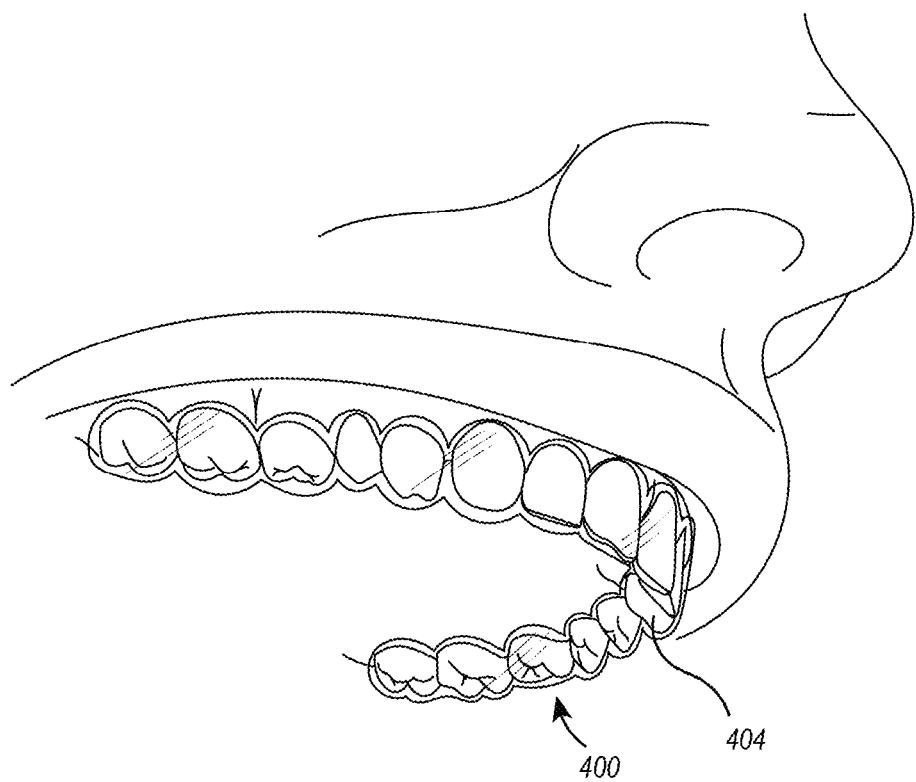
FIG. 4 illustrates a dental delivery system utilizing a custom dental tray after it has been placed over teeth of a dental arch causing the curable composition to conform thereto.

As shown in FIG. 4, a dental treatment system 400 may utilize a custom dental tray 404 having a shape and contour corresponding to the teeth and dental arch of a user. The whitening composition 102 may be mixed and disposed in the custom dental tray 404 prior to placing it over the teeth as described with respect to FIGS. 1-3.

Figure 5A:
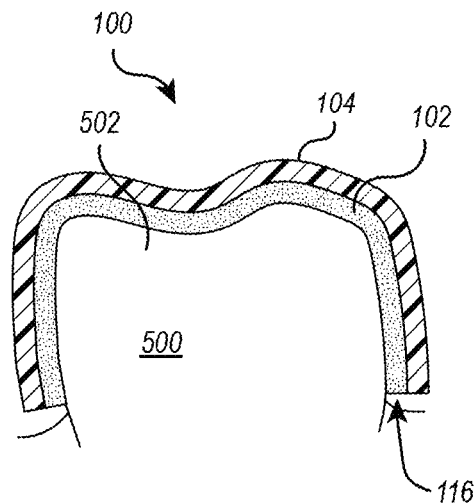
FIGS. 5A and 5B illustrate cross-sectional views of the dental delivery system overlying teeth.
Figure 5B:
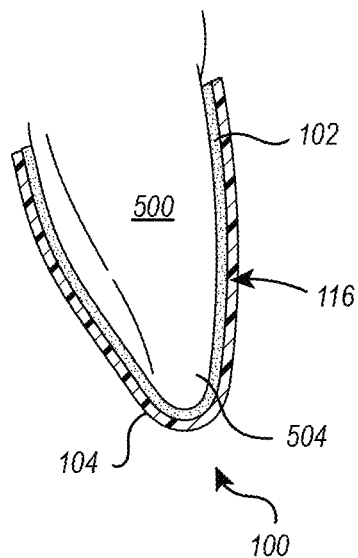

FIGS. 5A and 5B illustrate a cross-sectional view of the dental whitening system 100 including the dental whitening composition 102 in the dental tray 104 once shaped by placement over teeth 500. For example, the whitening composition 102, upon curing, may form a cohesive elastomeric material conformed to the teeth 500 that acts as a network or membrane 116 which adheres to and stays in contact with the teeth 500. The membrane 116 of the hardened material may behave as a unified body or aggregate that is no longer in a fluid or flowable state. As illustrated in FIGS. 5A and 5B, the membrane 116 overlies and conforms to the shape of teeth 500, such as over occlusal surfaces 502 and incisal surfaces 504 of teeth 500.

The whitening composition 102 conforms to and contacts surfaces of the teeth 500, enabling whitening agents dispersed throughout the whitening composition 102 to diffuse out and directly contact surfaces 502 and 504 providing sustained whitening (e.g., cosmetic whitening). The whitening composition 102 may have a thickness in a range of about 0.5 mm to about 5 mm, and typically between 1 mm and 2 mm, and may be varied. The whitening composition 102 may substantially surround outer surfaces 502 and 504 of the teeth 500, as shown in FIGS. 5A and 5B, or may at least partially contact outer surfaces 502 and 504. Once cured, the hardened whitening composition 102 will maintain its position adhered to teeth 500. The tray 104 provides additional support for the whitening composition 102 during and after the curing process and protects surrounding tissues (not shown) from being exposed to compounds diffusing out of the whitening composition 102, such as oxygen, whitening agents, and/or desensitizing agents.

The tray 104 together with the whitening composition 102 closely fits around the teeth 500 as the whitening composition 102 cures into the network or membrane 116 of elastomeric material. Prior to curing, the close fit against the teeth 500 reduces the risk of the whitening composition 102 (and the whitening agents contained therein) leaking or being expressed out of the tray 104 and onto the gums and oral tissues of the user, potentially causing irritation due to the whitening agents coming into direct contact with softer tissues. After curing, the network or membrane 116 of hardened whitening composition 102 is substantially immobile and remains in place and adhered to teeth with or without the tray 104. Thus, the whitening composition 102 reduces or eliminates the risk of irritation or damage that may be caused by conventional, non-hardening whitening gels that may leak or ooze out of the dental tray during treatment. By maintaining its position and reducing the risk of irritation caused by displaced treatment agent, the whitening composition 102 provides increased contact with teeth and extended wear time in comparison to conventional dental whitening gels.

As the whitening composition 102 undergoes condensation curing, a transition between a flowable and/or fluid gel-like state and to a solid and/or rubber-like state occurs. In the fluid state, the whitening composition 102 is capable of flowing into spaces, voids and contours in contact surfaces of the teeth and dental arch enabling formation of a reverse image of such structures during curing. Once sufficiently cured, the whitening composition 102 has transitioned from the fluid gel-like state to the rubber-like state as a consolidated, single-piece silicone elastomer material that mirrors and conforms to the tooth and dental arch structure forming the membrane 116. As described in further detail below, the cured membrane 116 may include a matrix having regions of the un-crosslinked materials throughout a cross-linked polymer material. For example, the carrier material having the whitening agent and other ingredients dispersed therein may form regions within cured polyvinylsiloxane material.

In some embodiments, the length of curing time for the whitening composition 102 ranges from 30 seconds to a length of treatment time, where the predetermined length of treatment time could be overnight (for example, 10 hours). In some embodiments, the length of curing time for the whitening material 102 ranges from 1 minute to 1 hour, more particularly from 3 minutes to 45 minutes, and even more particularly from 5 minutes to 30 minutes. In some embodiments, the whitening composition 102 may be configured such that the curing process is not complete until a desired amount of the whitening agent has been gradually released therefrom. In this embodiment, a user would know the whitening treatment has finished when the whitening composition 102 has finished curing into a unified network or solid (e.g., reached a hardened state or is easily releasable from teeth). In some embodiments, the set time for the whitening composition 102 (that is, how long it takes the whitening composition 102 to cure and harden) is a function of the concentration of at least one of the whitening agents (e.g., peroxides) and/or condensation catalysts present in the whitening composition 102.

Optionally, the tray 104 may be removed, leaving only the whitening composition 102 over teeth once it has sufficiently cured. However, it may be desirable to keep the tray 104 in place to assist in maintaining the dental whitening agent against the teeth, to prevent compounds from diffusing out of the whitening composition 102 into a user's mouth, and to facilitate in removal and replacement of the whitening composition 102.

Figure 6:
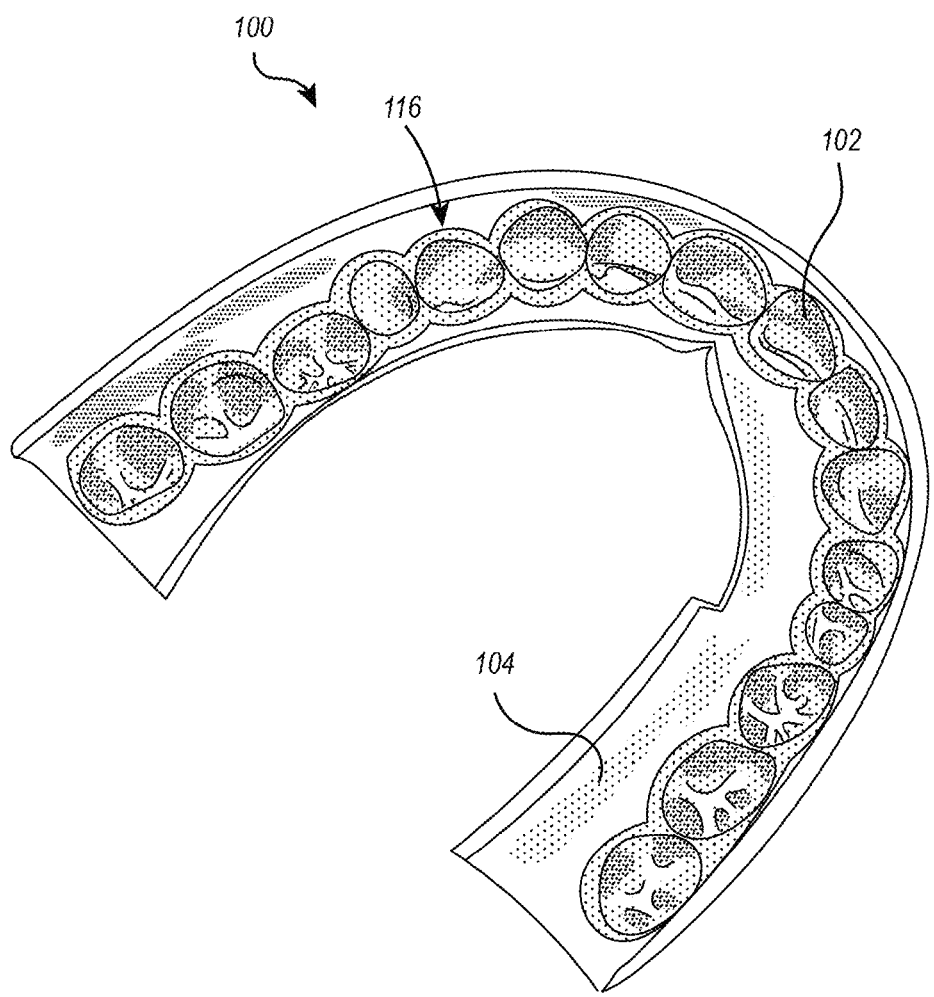
FIG. 6 illustrates the dental delivery system having a hardened whitening composition therein.

Referring to FIG. 6, once the whitening composition 102 has sufficiently hardened, it may be readily removed from the teeth (not shown). The cured whitening composition 102 includes a three-dimensional matrix within which the whitening agents and optional additives are dispersed and from which the whitening agents and optional additives gradually diffuse out. In some embodiments, the matrix is a polymer matrix that may include, for example, a silicone matrix having the other ingredients (e.g., whitening agent, additives, carrier materials, etc.) dispersed therein. For example, the whitening agent may be a peroxide-based whitening agent and may be present in the whitening composition 102 in a concentration of between about 1% and about 90%, such as for example, between about 6% and about 60%, between about 10% and about 50%, or between about 20% and 40%. In some embodiments, the whitening agent is a mixture of hydrogen peroxide and carbamide peroxide and is present in the whitening composition 102 in in a total combined concentration in a range of between 6% and 50%. The gradual release of the whitening agent enables increased concentrations of whitening agent to be incorporated in comparison to conventional whitening gels. Such increased concentrations may allow for greater whitening efficacy with fewer treatments. The gradual release of the peroxides and molecular oxygen from the cured whitening composition 102 may substantially reduce or eliminate tooth and tissue sensitivity associated with conventional peroxide tooth whitening, especially in increased concentrations. It also provides for extended treatment times, including after removing and reinstalling the elastomeric whitening material one or more times.

The matrix forms as a result of the curing process. The carrier material (e.g., polyacrylic acid) in the whitening composition 102 promotes even mixing of the ingredients therein to facilitate uniform polymerization and a homogeneous, hardening composition and, thus, uniform distribution of treatment agents (e.g., whitening, desensitization or remineralizing agents) within the matrix. The carrier material may have increased hydrophilicity in comparison to the silicone polymers and may, thus, increase hydrophilicity of the cured matrix of whitening composition 102 and improve the accuracy of the impression created as the material cures. Furthermore, the matrix may include regions of the more hydrophilic, un-crosslinked carrier material (having the whitening material disposed therein) within the more hydrophobic, crosslinked polyvinylsiloxane material. It has been observed that, in the absence of a carrier material such as polyacrylic acid, two-part whitening compositions formulated from a hardening polyvinylsiloxane material may not efficiently release the whitening agent due to immobilization of the whitening agent within the cured polyvinylsiloxane matrix. This is especially true in the case of solid whitening agents, such as carbamide peroxide.

In the cured matrix, the more hydrophilic nature of the carrier material may facilitate diffusion of the whitening agent out of the matrix and onto the teeth in the presence of water (e.g., saliva). Thus, the whitening agents of the whitening composition 102 exhibit a gradual release over time. This behavior may exist whether the bleaching agent is hydrogen peroxide or carbamide peroxide or a combination of the two. As the whitening composition 102 cures against teeth, the whitening agent and/or oxygen slowly diffuses out of the matrix and contacts the teeth to promote whitening (e.g., cosmetic whitening).

The cured whitening composition 102 may be temporarily removed from teeth and later replaced without having to discard the treatment composition. The gradual release of dental bleaching agent by the matrix reduces the risk of sensitivity that would otherwise be caused by the fast release of highly concentrated peroxide in the absence of the matrix, despite the high concentrations of peroxide present in the cured whitening material 102. This diffusion continues even after curing of the whitening composition 102 has been completed and will continue until a substantial portion of the bleaching agent has been diffused out of the matrix of the cured whitening composition 102. The gradual release allows a user to use the whitening composition 102 for longer periods of time before the effectiveness of the whitening material 102 begins to decline. In some embodiments, the whitening composition 102 is configured to harden into an elastomeric solid. The hardened composition 102 stays in place where treatment is desired rather than diffusing or migrating to other parts of the mouth or being prematurely spit out.

The elastomeric behavior of the whitening composition 102 enables removal of the hardened whitening composition 102 without leaving a significant amount of the composition or residue on the teeth or other oral tissue(s). Surprisingly, it has been found that the whitening composition 102 has good adhesion the teeth during treatment, but preferentially adheres to conventional tray or barrier materials, such as those formed from polymers, waxes, or combinations thereof. The whitening composition 102 will preferentially adhere to custom or non-custom dental trays. Thus, use of a tray or barrier material, such as dental tray 104, facilitates removal of the whitening composition 102 by providing a support material to which the whitening composition 102 remains adhered during removal from the teeth. The hardened whitening composition 102 containing the impression of the teeth and dental arch may be reapplied by the user to the original site of application. Such reuse or reapplication of the whitening composition 102 allows the user to pause the whitening treatment (e.g., cosmetic whitening) and continue it after a break by simply removing the hardened whitening composition 102 and later replacing it over the teeth.

Figure 7:
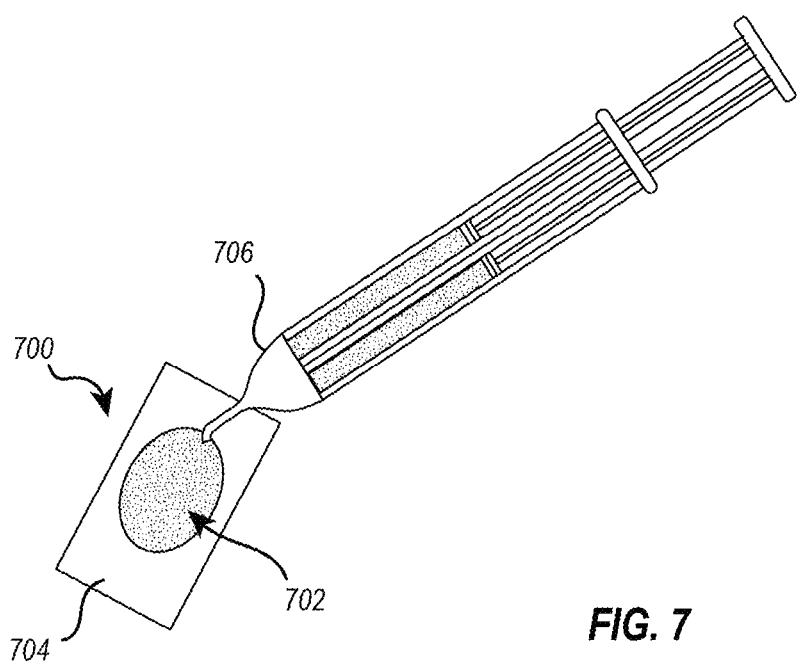
FIG. 7 illustrates an example of a curable treatment composition being dispensed from a dual barrel mixing syringe to a backing material.

As shown in FIG. 7, an oral delivery system 700 may be formed by applying a hardening composition 702 as described herein to a backing material or strip 704 while the hardening composition 702 is in a flowable state. The backing material 704 may be formed from any material suitable for carrying the hardening material such that it may be applied to the oral tissue. For example, the backing material 704 may be a material that is substantially impermeable to water, saliva, and/or one or more materials in the hardening composition 702 (e.g., functional agents or active ingredients). Examples of suitable materials for the backing material 704 include those described with respect to the liner 110 illustrated in FIG. 1. The liner 704 may be substantially flexible to allow the liner and composition to conform to oral tissues during application and hardening. For example, the backing material 704 may have a thickness of less than about 2 mm, such as between about 0.3 mm and about 1 mm. The hardening composition 702 may include a curable or hardening systems having a viscous carrier and a functional agent therein. As shown in FIG. 7, the hardening composition 702 be a two-part composition containing a catalyst in one part and reactive polymers in the other part. The hardening composition 702 may be mixed and disposed on the barrier material 704 using any method, such as using a dual barrel syringe 706 as described with respect to FIG. 2. Once dispensed, the hardening composition 702 may be applied to oral tissue while still in a flowable or semi-flowable state. The backing material 704 may act as a support for the hardening composition, isolating the hardening composition 702 to specific oral tissues while preventing leaching of the functional agent(s) to surrounding oral tissues.

Figure 8A:
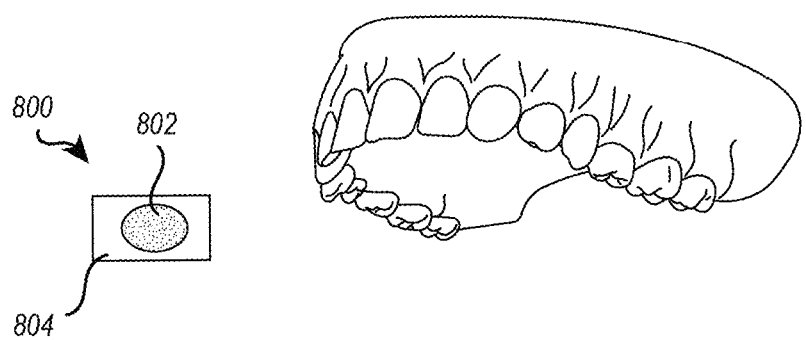
FIGS. 8A-8C illustrate an example of applying a curable treatment composition to oral tissue using a backing material to deliver one or more functional agents to such oral tissue.
Figure 8B:
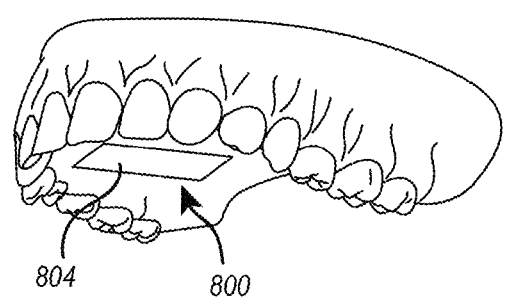
Figure 8C:
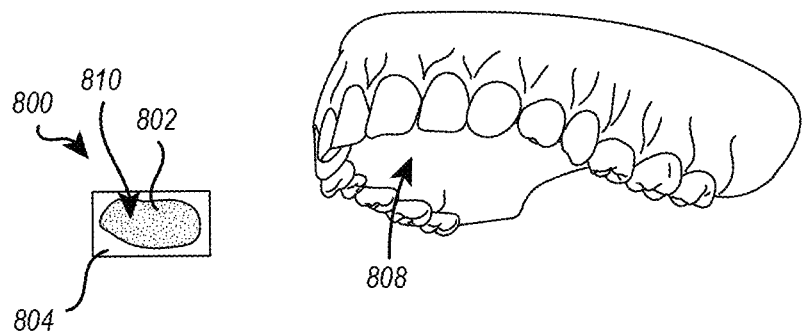

As shown in FIG. 8A-8C, an oral delivery system 800 including a quantity of hardening composition 802 disposed on a backing material 804, such as the oral delivery system 700 described with respect to FIG. 7, may be removably adhered to oral tissue 808. Referring to FIG. 8A, the hardening material 802 may be in a flowable state wherein the materials therein have not fully cured.

The backing material 804 may facilitate placement of the system 800 onto a desired region of the oral tissue 808. Once placed, the system 800 may optionally be held in place for a sufficient amount of time to allow the hardening material 802 to at least partially harden. The hardened or partially hardened composition 802 may have improved adherence to the oral tissue 808 such that the composition 802 (and optional backing material 804) can remain on the oral tissue without additional support, as shown in FIG. 8B.

The oral delivery system 800 may be placed on any region(s) of oral tissue 808 when the hardening composition 802 is still in an at least partially flowable state and, once at least partially hardened, can be removed easily and with the hardened composition 802 generally in a single piece, as shown in FIG. 8C. The hardened composition 802 may form an impression or imprint 810 of the oral tissue 808 therein. Additionally, the system 800 may be removed and replaced on the same region or a different region of the oral tissue to enable delivery to be delayed, performed intermittently, and/or at different regions using a single quantity of the composition 802.

Figure 9:
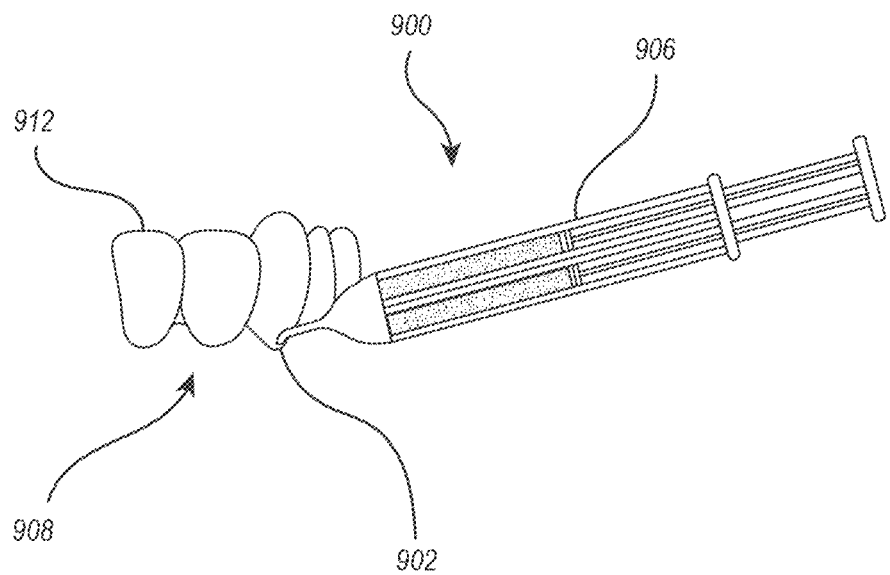
FIG. 9 illustrates an example of a curable treatment composition being applied to the gingival margin between teeth and gums.

FIG. 9 illustrates another example of a method of oral delivery application of a hardening composition 902 as described herein directly to gums 908 using a delivery syringe 906. After application, the composition 902 will harden to a state that is able to maintain shape and integrity in the oral environment and will remain adhered to oral tissue, such as the gums 906, until removed by the user. In the hardened state, the composition 902 provides improved comfort, ease, removal, and reattachment in comparison to compositions that remain in a viscous or flowable state.

Figure 10:
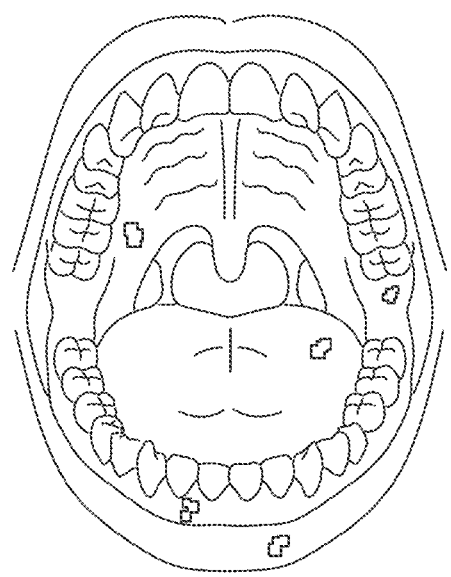
FIG. 10 illustrates examples of areas of soft oral tissues on which the curable treatment compositions of the disclosure may be applied.

Referring to FIG. 10, the presently disclosed oral delivery compositions are suitable for delivery to any regions of the oral tissue, such as the cheeks, buccal tissue, gums, lips, palette, teeth, etc.

While examples herein illustrate delivery of two-part hardening compositions using a mixing delivery syringe, it is to be understood that the hardening compositions disclosed herein may also be one part and may be mixed and delivered using suitable means. Furthermore, the hardened compositions including functional materials disclosed herein may be easily removed from oral tissues simply by peeling away the backing material or the hardened material itself, and may later be reapplied.

By way of example and not limitation, FIG. 10 shows areas of oral tissue on which the present hardening compositions may be applied to deliver any desired functional compositions. As previously described, the hardening composition may be applied using any delivery vehicle, such as an oral tray or strip.

In order to more clearly illustrate the parameters of the disclosed dental whitening materials within the scope of the present disclosure, the following examples are presented. The following examples are intended to be exemplary and should not be viewed as limiting the scope of the disclosure.

Example 1

For comparative purposes, whitening materials were prepared without a carrier material by combining the ingredients shown in Tables 1A and 1B.

TABLE 1A

Composition of Whitening Formulation A

| Formulation A | ~3 g | g | Function |
|---|---|---|---|
| Vinyltriisopropenoxysilane | 0.200 | 0.202 | Silicate ester |
| Silanol-terminated polydimethylsiloxane | 2.500 | 2.495 | Hydroxy-end-stopped polydimethylsiloxane |
| Dimethyldieodecanoatetin | 0.100 | 0.099 | Tin-based condensation catalyst |

TABLE 1A-continued

Composition of Whitening Formulation A

| Formulation A | ~3 g | g | Function |
|---|---|---|---|
| Fumed silica | 0.300 | 0.301 | Silica filler |
| Hydrogen peroxide (50% solution) | 0.350 | 0.344 | Whitening additive |

TABLE 1B

Composition of Whitening Formulation B

| Formulation B | ~3 g | g | Function |
|---|---|---|---|
| Vinyltriisopropenoxysilane | 0.200 | 0.204 | Silicate ester |
| Silanol-terminated polydimethylsiloxane | 2.500 | 2.495 | Hydroxy-end-stopped polydimethylsiloxane |
| Dimethyldieodecanoatetin | 0.100 | 0.103 | Tin-based condensation catalyst |
| Fumed silica | 0.300 | 0.298 | Silica filler |
| Carbamide peroxide | 0.350 | 0.353 | Whitening additive |

Processing Order:
1. Combine dimethyldieodecanoatetin and silanol-terminated polydimethylsiloxane;
2. Add fumed silica;
3. Add 50% hydrogen peroxide solution; and
4. Add vinyltriisopropenoxysilane.

Results

After sufficient cure time, physical properties of and distribution of materials within Formulations A and B were observed. Formulation A cured to a suitable hardened state, but it was observed that the cured material was damp because the hydrogen peroxide did not sufficiently incorporate into the material. Formulation B cured to a hardened state, but it was observed that the carbamide peroxide was not uniformly dispersed or incorporated throughout the material. Thus, it was demonstrated that liquid or solid actives/whitening agents (i.e., hydrogen peroxide solution and carbamide peroxide) are not easily incorporated into a curable polymer system, such as a polyvinylsiloxane system, in the absence of a carrier material (e.g., hydrophilic polymer).

Example 2

A study was performed to determine compatibility of functional silane fluids (e.g., silicate esters) and condensation catalysts (e.g., tin-based compounds). Sample gels were prepared containing a mixture of silane fluid and tin-based catalyst to determine their direct compatibility. The concentration of the catalyst was included in a range of 1% to 20% by weight, and the concentration of the silane was in a range of 80% to 99% by weight. After mixing, the sample gels were placed at room temperature (25° C.) and 40° C.

Discoloration of samples placed at 40° C. containing higher concentrations of catalyst were observed within 96 hours. The two samples with the highest concentrations of catalyst had polymerized within 96 hours. Remaining samples continued to discolor and polymerize with time.

It was observed that sample gels with increased catalyst concentrations cured more rapidly. The higher the catalyst concentration, the faster the premature cure. Thus, it was demonstrated that the curing time of the compositions can be a function of the concentration of the condensation catalyst.

It was observed that compositions containing both a polymerizable material (e.g., functional silane or siloxane) and a condensation catalyst autocatalyzed over time and were, thus, unstable at both room temperature and 40° C. It was concluded that storing the catalyst with polymerizable materials, such as the silane material or siloxane material, resulted in premature curing compromising commercial viability. Separating the polymerizable materials and the catalyst into different parts in accordance with the present invention substantially improves stability of compositions including the two ingredients and provides a commercially viable composition.

Example 3

Experimental formulations were made according to Table 3 to replicate comparative two-part gel systems incorporating a peroxide whitening agent.

TABLE 3

Formulation of Components A and B of Comparative Gel

| Component A | Component B |
|---|---|
| Hydroxy-end-stopped polydimethylsiloxanes (reactive polymers) | Silicate esters (crosslinker) |
| Peroxide whitening agent | Condensation catalyst |
| Fillers and other auxiliaries/additives | Optional auxiliaries and additives |
| Small amounts of H$_2$O | Paste formers/viscosity adjusters |

The ingredients of Components A and B were combined to form the two parts of the comparative gel system and the two parts were observed over time. In Component A, the polydimethylsiloxanes and water or water-based solutions (e.g., hydrogen peroxide) separated out of the mixture shortly after mixing the ingredients together using established manufacturing methods. In Component B, placing the silicate ester and condensation catalyst in the same mixture caused premature curing in the presence of moisture. This premature curing behavior was observed in the presence of water sources as small as ambient moisture or environmental humidity. It was concluded that a two-part whitening system with the experimental formulations are not commercially viable. Specifically, it was demonstrated that formulations including a mixture of a curable polymer (e.g., polydimethylsiloxanes) and a whitening agent were not stable in the absence of a carrier material as the whitening agent separated out of the mixture. It was also demonstrated that formulations including a mixture of crosslinkers (e.g., silicate esters) and catalysts were not stable due to premature curing. Thus, both Components A and B of the experimental formulation failed to produce commercially viable results for different reasons. The inventive hardening composition solves the demonstrated stability issues by providing a carrier material for materials prone to separating out of the mixture (e.g., whitening agent) and by separating the catalyst and polymerizable materials (e.g., the crosslinker) into different parts until use.

Example 4

Figure 11A:
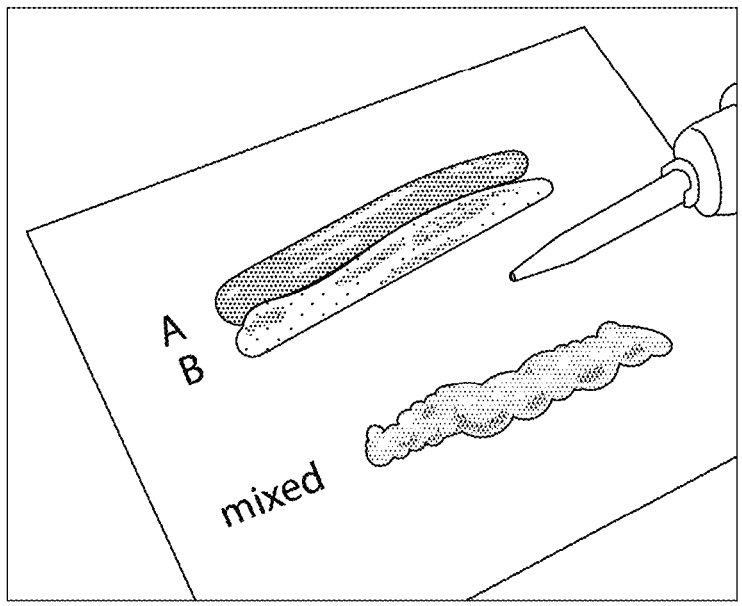
FIGS. 11A-11C illustrate an example of hardening behavior and subsequent flexibility and resilience of an exemplary two-component dental treatment composition.
Figure 11B:
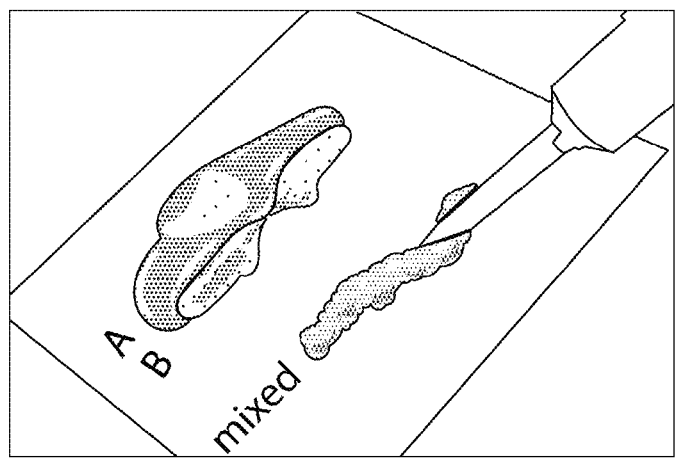
Figure 11C:
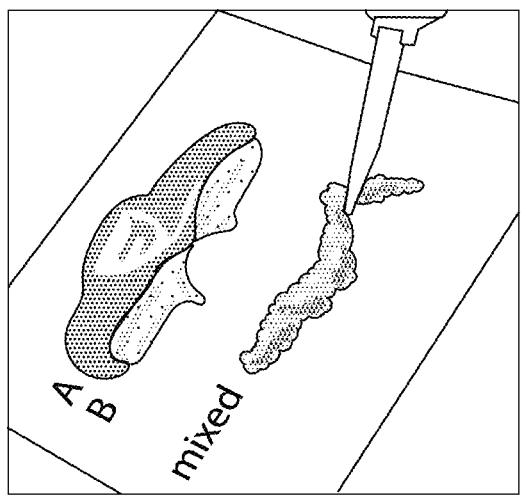

FIGS. 11A-11C illustrate testing of hardening behavior and substantially uniform mixing of an exemplary two-component dental whitening material. Each component A and B was prepared according to disclosed methods. The ingredients of components A and B are listed in Table 4.

TABLE 4

Formulations of Components A and B of Whitening Material

| Component A | Component B |
|---|---|
| Hydroxy-end-stopped polydimethylsiloxanes | Whitening substances |
| Silicate esters | Condensation catalyst |
| Viscosity adjusting additives | Support material and auxiliaries |
| Blue colorant | Viscosity adjusters and other additives |

The individual components of the two-part dental whitening material were tested against a mixture of the two components separately, as shown in FIGS. 11A-11C. The mixture was expressed through a mixing tip and as shown, the two parts were combined in a substantially homogeneous manner. The individual components and the mixture were still malleable as the curing process had just started, as shown in FIG. 11B. After a sufficient setting time, the individual components were still completely malleable whereas the mixture had turned into an elastomeric solid, as shown in FIG. 11C.

Example 5

FIGS. 12A-13C illustrate examples of removal and reapplication of a hardened dental whitening gel to a typodont using different tray types and materials for application. A two-part curable whitening gel was formulated with the ingredients shown in Table 5.

TABLE 5

Formulation of Components A and B of Whitening Gel

| Component A | Component B |
|---|---|
| Silicate esters | Whitening substances |
| Hydroxy-end-stopped polydimethylsiloxanes | Condensation catalyst |
| Viscosity adjusting additives | Support material and auxiliaries |
| Blue colorant | Viscosity adjusters and other additives |

Figure 12A:
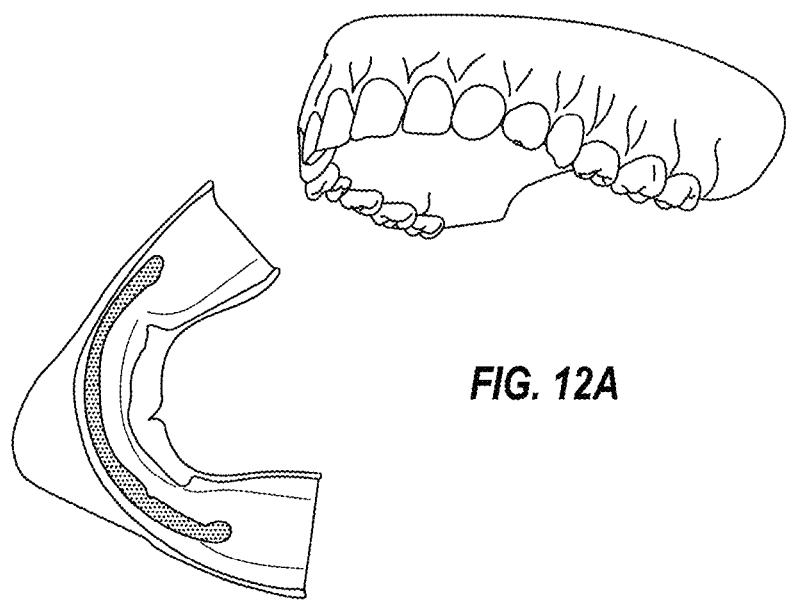
FIGS. 12A-13C illustrate an example of application, removal, and reapplication of a cured whitening composition material to and from a user's teeth.
Figure 12B:
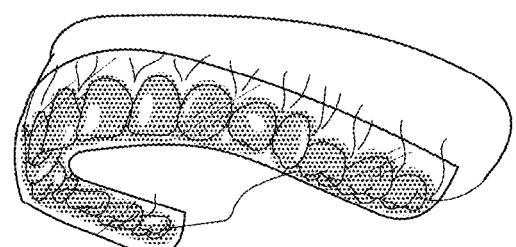
Figure 13A:
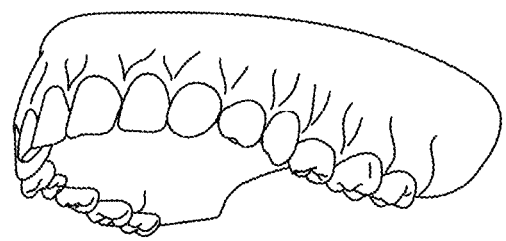
Figure 13A:
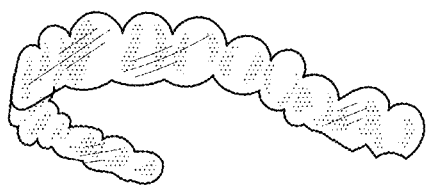
Figure 13B:
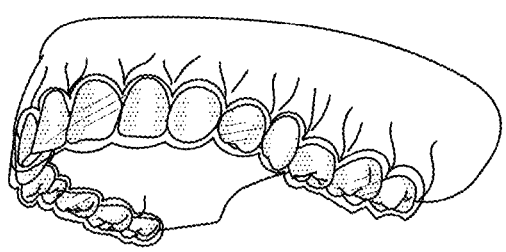

One part (Component A) of the dental whitening gel was dyed to enable observation of mixing between the two parts. The dental whitening gel was expressed through a mixing tip into both a disposable tray (FIG. 12A) and a custom-fitted tray (FIG. 13A) at separate intervals. The disposable tray was formed from a flexible wax-polymer material and included a removable outer support tray while the customized tray was formed from a more rigid polymer material. The dental whitening gel was applied to each typodont by placing the disposable or custom tray containing the gel onto the teeth of the typodont, as shown in FIGS. 12B and 13B, and leaving the whitening system on the typodont undisturbed for a predetermined setting time of 5 to 10 minutes.

Figure 12C:
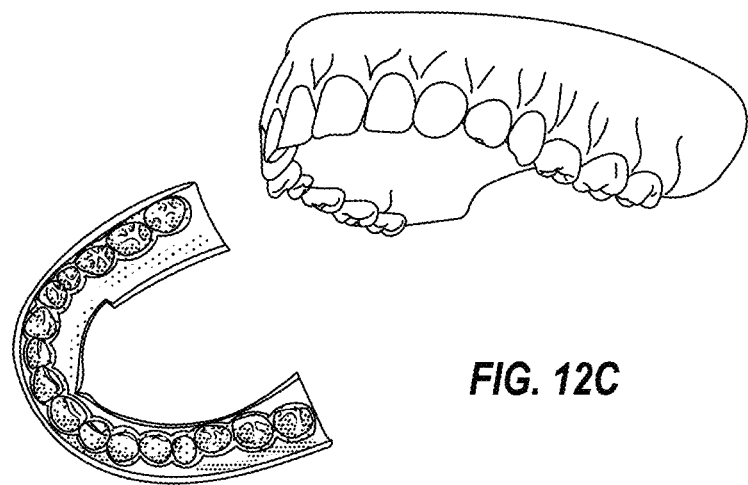
Figure 13C:
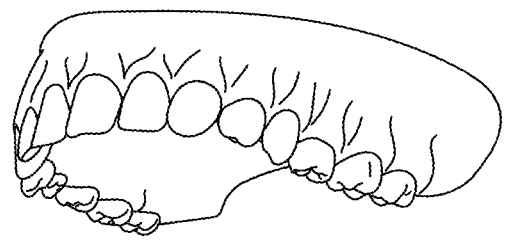
Figure 13C:
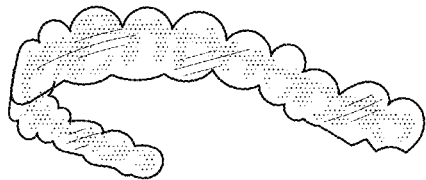

After the setting time had elapsed, the trays were removed from the typodont, as shown in FIGS. 12C and 13C. No whitening gel was observed on the teeth or typodont after treatment in either instance (see FIG. 12C) demonstrating that the cured gel preferentially adheres to the trays. As shown in FIG. 12C, the whitening gel remained adhered to the tray material and maintained the shape of the teeth after removal; that is the whitening gel mirrored the geometry of the typodont. The trays were then replaced on the dentifrice to verify that it could be fitted back to the dentition. In both instances, the whitening gel was found to fit back into place where it had previously been applied. It was concluded that the hardened whitening gel readily detaches from teeth (possibly due to surface moisture) and preferentially sticks to polymer-based and wax-based tray materials. Furthermore, it was observed that the tray including the hardened whitening gel could be readily removed and reapplied to teeth enabling reuse of the whitening material.

Example 6

Tables 6A and 6B show an example of cosmetic whitening efficacy using the disclosed system. Extracted human teeth were artificially stained using a mixture of red wine and blueberry and pomegranate juice. The teeth were immersed in the mixture and stored at 40° C. for 2 weeks and 6 weeks. After staining, the teeth were removed from the mixture and were rehydrated in water for at least one week before application of any whitening gels. The resulting stains on the teeth were dark purple to brown in the dentin and gray to red brown in the enamel. As described below, three comparative studies were conducted to compare the effects of treatment of the stained sample teeth with hardening whitening gels according to embodiments described herein, water, and conventional non-hardening whitening gels. To evaluate whitening (cosmetic effect on shade change) in the teeth, the teeth were evaluated using a VITA® shade guide according to the instructions for use. The general formulations of the hardening and non-hardening whitening gels are shown in Tables 6A and 6B below.

TABLE 6A

Formulation of Components A and B of Hardening Gel

| Component A | Component B |
|---|---|
| Silicate esters | Carbamide peroxide |
| Hydroxy-end-stopped polydimethylsiloxanes | Condensation catalyst |
| Viscosity adjusting additives | Support material and auxiliaries Viscosity adjusters and other additives |

TABLE 6B

General Formulation of Comparative Gel

| Gel Formula |
|---|
| Carbamide peroxide |
| Support material and auxiliaries |
| Viscosity adjusters and other additives |

The first study compared the effect on tooth shade of multiple applications of a hardening whitening gel containing 10% carbamide peroxide by weight against a control of water. The hardening whitening gel and water were applied to different stained, rehydrated teeth (Tooth A and Tooth B, respectively) in 8-hour intervals at 40° C. for a total of ten applications per tooth. The teeth were rehydrated with water overnight between each of the ten applications. Before evaluation for shade change, the teeth were rehydrated in water for over 24-hours after the final application to ensure changes in color were not caused by dehydration. The results of the evaluation are shown in Table 6C.

TABLE 6C

Shade Change - Comparative Study 1

| 8-hour applications | Tooth A - Water (0% carbamide peroxide) | | Tooth B - Hardening Gel (10 wt % carbamide peroxide) | |
|---|---|---|---|---|
| | 2-week stain | 6-week stain | 2-week stain | 6-week stain |
| Before | C4 | A4 | D3 | A4 |
| Midpoint | C4 | A4 | A1 | A2 |
| After | C4 | A4 | B1 | B1 |

As shown in Table 6C, the inventive hardening whitening gel was found to whiten more effective than the control, water, which had no effect on teeth.

The second study compared multiple applications of a hardening whitening gel with a conventional, non-hardening whitening gel, containing equal concentrations of carbamide peroxide. The hardening whitening gel and the conventional whitening gel both contained 35% carbamide peroxide by weight and were applied to different stained, rehydrated teeth (Tooth C and Tooth D, respectively) in 1-hour intervals at 40° C. for a total of ten applications per tooth. The teeth were rehydrated for at least one hour between each of the ten applications. Before evaluation for shade change, the teeth were rehydrated in water for over 24-hours after the final application to ensure changes in color were not caused by dehydration. The results are shown in Table 6D.

TABLE 6D

Tooth Shade Change - Comparative Study 2

| 1-hour applications | Tooth C - Hardening Gel (35 wt % carbamide peroxide) | | Tooth D - Conventional Gel (35 wt % carbamide peroxide) | |
|---|---|---|---|---|
| | 2-week stain | 6-week stain | 2-week stain | 6-week stain |
| Initial | D3 | C4 | D3 | A4 |
| Midpoint | A3 | A2 | D2 | A3 |
| Final | A1 | B1 | D2 | A2 |

As shown in Table 6D, the hardening whitening gel was found to be equally or more effective in cosmetically whitening teeth than the conventional, non-hardening whitening gel.

The third study compared stained, rehydrated sample teeth treated with water, hardening gels according to embodiments described herein, and conventional, non-hardening whitening gel during a single application. For the hardening and conventional whitening gels, formulations containing 35% and 10% by weight carbamide peroxide were used. In this study, teeth were exposed to their respective whitening gel for 24-hours at 40° C. The teeth were rehydrated for an additional 24-hours before being evaluated for shade changes. The results are shown in Table 6E.

TABLE 6E

Tooth Shade Change - Comparative Study 3

| 24-hour application | Water (0% carbamide peroxide) | | Hardening Gel (10% carbamide peroxide) | |
|---|---|---|---|---|
| | 2-week stain | 6-week stain | 2-week stain | 6-week stain |
| Before | D3 | A4 | C2 | C4 |
| After | D3 | A4 | A2 | C2 |

| 24-hour application | Conventional gel (35% carbamide peroxide) | | Hardening gel (35% carbamide peroxide) | |
|---|---|---|---|---|
| | 2-week stain | 6-week stain | 2-week stain | 6-week stain |
| Before | C1 | C4 | A3.5 | C4 |
| After | A1 | C1 | A2 | C2 |

As shown in Table 6E, the hardening whitening gels were found to be effective in cosmetically whitening teeth in comparison to the convention whitening gel and the water, which had no effect on the shade of teeth.

Example 7

The peroxide release behavior of hardening whitening compositions and conventional, non-hardening whitening compositions was characterized using peroxide assays. Uncured composition was added directly to a flask after mixing to determine the full concentration of the peroxides. For elution testing, samples of the composition were allowed to set. Once cured, the solid composition was then added to the flask and allowed to elute for a predetermined amount of time. The disclosed whitening gel showed a gradual release of the peroxides over several hours of elution. The peroxide release behavior was comparatively studied by measuring the dispersion rate of peroxide out of each composition.

TABLE 11A

Formulation C: carbamide peroxide in silicone-only composition (without polyacrylic acid)

| Sample ID | Peroxide content (% m/m) |
|---|---|
| Dispersion | 7.72 ± 3.67 |
| 5 min | 0.30 ± 0.09 |
| 15 min | 0.65 ± 0.08 |
| 1 hour | 1.61 ± 0.96 |

TABLE 11B

Formulation D: Carbamide peroxide in inventive composition containing silicone and polyacrylic acid

| Sample ID | Peroxide content (% m/m) |
|---|---|
| Dispersion | 10.31 ± 0.33 |
| 5 min | 0.75 ± 0.04 |
| 15 min | 2.01 ± 0.09 |
| 1 hour | 6.65 ± 0.54 |
| 2 hours | 8.77 ± 0.78 |
| 4 hours | 9.47 ± 0.33 |
| 24 hours | 9.57 ± 0.09 |

TABLE 11C

Formulation E: Hydrogen peroxide in silicone-
only composition (without polyacrylic acid)

| Sample ID | Peroxide content (% m/m) |
|---|---|
| Dispersion | 26.76 ± 0.83 |
| 5 min | 7.41 ± 0.70 |
| 15 min | 12.18 ± 1.10 |
| 1 hour | 20.49 ± 0.56 |

TABLE 7D

Formulation F: Hydrogen peroxide in inventive composition
containing silicone and polyacrylic acid

| Sample ID | Peroxide content (% m/m) |
|---|---|
| Dispersion | 10.88 ± 0.05 |
| 5 min | 1.58 ± 0.16 |
| 15 min | 3.72 ± 0.07 |
| 1 hour | 5.25 ± 0.11 |

The results show that the peroxide release behavior of silicone-only compositions showed either an incomplete release or rapid release during curing. Thus, the silicone-only composition may not be suitable for the purposes of tooth whitening. When curing system included silicone combined with polyacrylic acid, as disclosed herein, a more gradual release of both peroxides was observed. Thus, the synergistic effect of combining the curable silicone system with a non-curing carrier, such as polyacrylic acid, unexpectedly slowed the release properties of the composition, which may provide better whitening results and reduced sensitivity.

Example 8

Release testing was performed to determine if non-whitening additives would mobilize from the polymerized matrix of the inventive hardening whitening gel, formulated according to Table 12A. Sodium fluoride (NaF), a fluoride ion source, was used as the example additive. In all testing instances, the hardening whitening gel was allowed to set completely before being placed in distilled water to elute. For both concentrations and at all elution times, fluoride ions were detected in the testing solution.

TABLE 12A

Formulation of Components A and B of Hardening Gel

| Component A | Component B |
|---|---|
| Silicate esters | Fluoride ion source |
| Hydroxy-end-stopped polydimethylsiloxanes | Condensation catalyst |
| Viscosity adjusting additives | Support material and auxiliaries |
| | Viscosity adjusters and other additives |

TABLE 12B1

Results of Elution of Hardening Gel in Water
Gel 1 - 0.25% w/w NaF when mixed

| Elution Time | Fluoride Ion (% w/w) |
|---|---|
| 30 minutes | 0.049 ± 0.008 |
| 1 hour | 0.053 ± 0.020 |
| 2 hours | 0.106 ± 0.010 |
| 4 hours | 0.123 ± 0.045 |

TABLE 12B2

Results of Elution of Hardening Gel in Water
Gel 2 - 5.0% w/w NaF when mixed

| Elution Time | Fluoride Ion (% w/w) |
|---|---|
| 30 minutes | 0.199 ± 0.037 |
| 1 hour | 0.240 ± 0.054 |
| 2 hours | 0.562 ± 0.142 |
| 4 hours | 0.614 ± 0.086 |

The results show that the presently disclosed hardening gel effectively releases fluoride ions, demonstrating the suitability of the gel for treating teeth with treatment agents, such as desensitizing agents.

Example 9

Testing was performed to characterize the hardening behavior of a two-part resin composition as disclosed herein and the release of a functional agent from such resin system once cured. Methacrylate resins were used as an exemplary hardening resin and the composition was formulated according to Table 13.

TABLE 13

Formulation of Components A and B of Hardening Gel

| Component A | Component B |
|---|---|
| Methacrylate resins | Carbamide peroxide |
| Light-activated initiator | Peroxide initiator |
| Amine synergist | Carrier material |
| Viscosity adjusting additives | Viscosity adjusters and other additives |

Equal parts of the individual components were mixed until substantially homogenous. The mixture was malleable at the beginning of the curing process, and after a sufficient setting time, had begun to form a semi-solid to solid material.

The exemplary hardening whitening composition was light cured using a dental curing light prior to being evaluated for peroxide release behavior. The mixture was malleable prior to being exposed to the dental curing light and had turned into a solid after exposure. Once cured, the solid composition was then added to a container of water and allowed to elute for a predetermined amount of time. The disclosed whitening gel showed a gradual release of peroxide over several hours of elution.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Additional Terms & Definitions

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may also include properties and/or features (e.g., ingredients, components, members, elements, parts, and/or portions) described in one or more separate embodiments and are not necessarily limited strictly to the features expressly described for that particular embodiment. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. A dental whitening system comprising:
a first part comprising: (i) a whitening agent, (ii) at least one of a catalyst that is not the whitening agent or an initiator that is not the whitening agent, and (iii) a carrier material, wherein the whitening agent and the at least one of the catalyst or the initiator are dispersed in the carrier material; and
a second part separate from the first part and comprising at least one of reactive monomer, a reactive oligomer, or a reactive polymer.

2. The dental whitening system of claim 1, wherein the whitening agent is at least one of hydrogen peroxide or carbamide peroxide.

3. The dental whitening system of claim 1, wherein the second part further comprises a crosslinker.

4. The dental whitening system of claim 1, wherein the carrier material comprises at least one of polyacrylic acid or polyvinylpyrrolidone.

5. The dental whitening system of claim 1, wherein the first part further comprises at least one additional treatment agent.

6. The dental whitening system of claim 5, wherein the at least one additional treatment agent comprises a desensitizing agent.

7. The dental whitening system of claim 1, wherein the second part comprises at least one silane-terminated siloxane or hydroxy-terminated siloxane and at least one silane crosslinker.

8. The dental whitening system of claim 1, wherein the first part is disposed in one barrel of a dual barrel syringe and the second part is disposed in another barrel of the dual barrel syringe.

9. The dental whitening system of claim 1, wherein the first part includes a catalyst, wherein the catalyst includes at least one of a tin compound or a platinum compound.

10. The dental whitening system of claim 1, wherein the first part includes a catalyst, wherein the catalyst includes a metal-organic catalyst.

11. The dental whitening system of claim 10, wherein the metal-organic catalyst includes at least one of dimethyldineodecanoatetin, bis(neodecanoate)tin, bis(2-ethylhexanoate) tin, di-n-butyldilauryltin, or dimethylhydroxy(oleate)tin.

12. A dental whitening material comprising:
a first part comprising: (i) a whitening agent, (ii) at least one of a catalyst that is not the whitening agent or initiator that is not the whitening agent, and (iii) a carrier material, wherein the whitening agent and the at least one of the catalyst or the initiator are dispersed in the carrier material; and
a second part comprising:
at least one of a reactive monomer, a reactive oligomer, or a reactive polymer, and
a crosslinker.

13. The dental whitening material of claim 12, wherein the carrier material is a water-soluble polymer.

14. The dental whitening material of claim 12, wherein the carrier material includes at least of a polyacrylic acid, polyvinylpyrrolidone, polyacrylate, polyacrylamide, polyacrylic acid-polyacrylamide copolymer, polyvinylpyrrolidone-vinyl acetate copolymer, polyvinyl alcohol, polyethylene oxide, polyvinyl caprolactam, glycerin, and/or poly (2-ethyl-2-oxazoline).

15. A dental whitening system comprising:
a tray having an arch shape and defining a channel; and
a dental whitening material for placement into the tray, wherein the dental whitening material comprises:
a first part comprising: (i) a whitening agent, (ii) a condensation catalyst that is not the whitening agent, and (iii) a carrier material, wherein the whitening agent and the condensation catalyst are dispersed in the carrier material; and
a second part comprising a siloxane and a crosslinker, wherein mixing the first and second parts causes the siloxane to condense and crosslink.

16. The dental whitening system of claim 15, wherein the siloxane comprises at least one of silanol-terminated polydimethylsiloxane or hydroxy-terminated polydimethylsiloxane.

17. The dental whitening system of claim 15, wherein the crosslinker comprises at least one functional silane.

18. The dental whitening system of claim 15, wherein the condensation catalyst comprises at least one of a tin compound or a platinum compound.

19. A method of cosmetically whitening teeth, comprising:
- providing a dental whitening system of claim 1;
- combining the first part and the second part to form a hardening composition;
- placing the hardening composition over at least a portion of a user's teeth;
- allowing the hardening composition to harden to form a hardened whitening composition on at least a portion of a user's teeth; and
- the hardened whitening composition providing a cosmetic tooth whitening effect.

20. The method of claim 19, further comprising:
- removing the hardened whitening composition from the user's teeth; and
- re-applying the hardened whitening composition to the user's teeth to resume cosmetic tooth whitening.

\* \* \* \* \*